United States Patent [19]
Dower et al.

[11] Patent Number: 6,140,493
[45] Date of Patent: Oct. 31, 2000

[54] METHOD OF SYNTHESIZING DIVERSE COLLECTIONS OF OLIGOMERS

[75] Inventors: William J. Dower, Menlo Park; Ronald W. Barrett, Sunnyvale; Mark A. Gallop, East Palo Alto; Michael C. Needels, Oakland, all of Calif.

[73] Assignee: Affymax Technologies N.V., Greenford, United Kingdom

[21] Appl. No.: 09/151,467

[22] Filed: Sep. 11, 1998

Related U.S. Application Data

[60] Continuation of application No. 08/473,676, Jun. 6, 1995, abandoned, which is a division of application No. 07/946,239, Sep. 16, 1992, Pat. No. 5,770,358, which is a continuation-in-part of application No. 07/762,522, Sep. 18, 1991, abandoned.

[51] Int. Cl.$^7$ ............................. C07H 21/00; B01J 20/26
[52] U.S. Cl. .................... 536/25.4; 536/25.41; 502/402; 502/413; 502/415; 502/416; 502/423; 502/425; 502/426; 502/427
[58] Field of Search .................................. 502/402, 413, 502/415, 416, 423, 425, 426, 427; 536/25.4, 25.41

[56] References Cited

U.S. PATENT DOCUMENTS

| | | |
|---|---|---|
| 4,182,654 | 1/1980 | Royer ...................................... 435/272 |
| 4,315,074 | 2/1982 | Royer ...................................... 435/70 |
| 4,471,072 | 9/1984 | Leyerle et al. ........................... 502/413 |
| 4,587,044 | 5/1986 | Miller et al. ............................. 530/211 |
| 4,631,211 | 12/1986 | Houghten ................................ 428/35 |
| 4,671,941 | 6/1987 | Niina et al. .............................. 422/131 |
| 4,701,304 | 10/1987 | Horn et al. ............................... 422/62 |
| 4,713,326 | 12/1987 | Dattagupta et al. ........................ 435/6 |
| 4,755,558 | 7/1988 | Kalbag ................................... 525/54.1 |
| 4,764,504 | 8/1988 | Johnson et al. ............................ 514/12 |
| 4,794,150 | 12/1988 | Steel ..................................... 525/54.11 |
| 4,818,681 | 4/1989 | Dattagupta ................................ 435/6 |
| 4,833,092 | 5/1989 | Geysen ................................... 436/501 |
| 4,855,225 | 8/1989 | Fung et al. ................................ 435/6 |
| 4,952,707 | 8/1990 | Edwards et al. ......................... 549/221 |
| 4,965,188 | 10/1990 | Mullis et al. .............................. 435/6 |
| 4,988,625 | 1/1991 | Marburg et al. ............................ 436/5 |
| 5,010,175 | 4/1991 | Rutter et al. ............................. 530/334 |
| 5,049,656 | 9/1991 | Lewis et al. ............................. 530/334 |
| 5,143,854 | 9/1992 | Pirrung et al. ........................... 436/518 |
| 5,221,736 | 6/1993 | Coolidge et al. ........................... 536/25 |
| 5,264,563 | 11/1993 | Huse ..................................... 536/25.3 |
| 5,324,483 | 6/1994 | Cody et al. ............................... 422/131 |

FOREIGN PATENT DOCUMENTS

| | | |
|---|---|---|
| 0 392 546 A2 | 12/1990 | European Pat. Off. . |
| WO 90/00626 | 1/1990 | WIPO . |
| WO 90/14441 | 11/1990 | WIPO . |
| WO 90/15070 | 12/1990 | WIPO . |
| WO 92/00091 | 1/1992 | WIPO . |
| WO 92/03461 | 3/1992 | WIPO . |
| WO 92/06176 | 4/1992 | WIPO . |
| WO 92/10092 | 6/1992 | WIPO . |
| WO 93/20242 | 10/1993 | WIPO . |
| WO 94/02515 | 2/1994 | WIPO . |
| WO 94/08051 | 4/1994 | WIPO . |

OTHER PUBLICATIONS

Shivikumar et al., Bull. Mater. Sci. , vol. 12, No. 1, pp. 27–32 (1989).

*Advances in Analytical Chemistry and Instrumentation*, Charles N. Reilley, Ed., John Wiley & Sons, Inc., 1964, pp. 56–59.

Arnold et al., Mar. 15, 1991, *Optics Letters* 16(6):420–422 Room–temperature microparticle–based persistent spectral hole burning memory.

Baldwin et al., 1990, *Tetrahedron* 46(19):6879–6884. New Photolabile phosphate protecting groups.

Barr et al., 1986, *BioTechniques* 4(5):428–432 7–Deaza–2'–deoxyguanosine–5'–triphosphate: Enhanced resolution in M13 dideoxy sequencing.

Bashkin et al., 1991, *J. Org. Chem.* 56:3168–3176 Synthesis and characterization of oligonucleotide peptides.

Borchardt et al., 1994, *J. Am. Chem. Soc.* 116:373–374 Synthetic receptor binding elucidated with an encoded combinatorial library.

Brenner et al., 1992, *Proc. Natl. Acad. Sci. USA* 89:5381–5383, Encoded combinatorial chemistry.

Crick et al., 1957, *Proc. Natl. Acad. Sci. USA* 43:416–421 Codes without commas.

Cwirla et al., 1990, *Proc. Natl. Acad. Sci. USA* 87:6378–6382 Peptides on phage: A vast library of peptides for identifying ligands.

Eritja et al., 1991, *Tetrahedron* 47(24):4113–4120 Synthesis of defined peptide–oligonucleotide hybrids containing a nuclear transport signal.

Fodor et al., 1991, *Science* 251:767–773 Light–directed, spatially addressable parallel chemical synthesis.

Frank and Doring, 1988, *Tetrahedron* 44(19):6031–6040, Simultaneous multiple peptide synthesis under continuous flow conditions on cellulose paper discs as segmental solid supports.

Frank et al., 1983, *Nuc. Acids. Res.* 11(13):4365–4377 A new general approach for the simultaneous chemical synthesis of large numbers of oligonucleotides: Segmental solid supports.

Frank et al., 1990, *Peptides* (Giralt & Andreu, eds., ESCOM Science Pub.), pp. 151–152 Facile and rapid 'spot–synthesis' of large numbers of peptides on membrane sheets.

Furka et al., Jul. 10–15, 1988, 14th Intl. Congress of Biochemistry, Prague, Czechoslovakia, Abstract No. Fr:013 Proteins and nucleic acids in three dimensions: Cornucopia of peptides by synthesis.

Furka et al., Aug. 15–19, 1988, Xth Intl. Symp. on Medicinal Chem., Budapest, Hungary, Abstract No. P–168, p. 288, More peptides by less labour.

(List continued on next page.)

*Primary Examiner*—James O. Wilson
*Attorney, Agent, or Firm*—Lauren L. Stevens

[57] ABSTRACT

A general stochastic method for synthesizing random oligomers can be used to synthesize compounds to screen for desired properties. The use of identification tags on the oligomers facilitates identification of oligomers with desired properties.

8 Claims, 13 Drawing Sheets

OTHER PUBLICATIONS

Furka et al., 1991, *Int. J. Peptide Protein Res.*, 37:487–493 General method for rapid synthesis of multicomponent peptide mixtures.

Geysen et al., 1987, *J. Immunol. Meth.*, 102:259–274 Strategies for epitope analysis using peptide synthesis.

Geysen et al., 1984, *Proc. Natl. Acad. Sci. USA*, 81:3998–4002 Use of peptide synthesis to probe viral antigens for epitopes to a resolution of a single amino acid.

Haralambidis et al., 1990, *Nuc. Acids Res.* 18(3):493–505 The synthesis of polyamide–oligonucleotide conjugate molecules.

Hayakawa et al., 1990, *J. Am. Chem. Soc.* 112:1691–1696 The allylic protection method in solid–phase oligonecleotide synthesis: An efficient preparation of solid–anchored DNA Oligomers.

Hodgson, 1992, *Bio/Technology* 10:973–974 Receptor screening and the search for new pharmaceuticals.

Houghten et al., 1991, *Nature* 354:84–86 Generation and use of synthetic peptide combinatorial libraries for basic research and drug discovery.

Houghten, 1985, *Proc. Natl. Acad. Sci. USA* 82:5131–5135 General method for the rapid solid–phase synthesis of large numbers of peptides: Specificity of antigen–antibody interaction at the level of individual amino acids.

Juby et al., 1991, *Tetrahedron Letters* 32(7):879–882 Facile preparation of 3' oligonucleotide–peptide conjugates.

Kaiser et al., 1989, *Science* 243:187–192 Peptide and protein synthesis by segment synthesis–condensation.

Kerr et al., 1993, *J. Am Chem Soc.*, 115:2529–2531 Encoded combinatorial peptide libraries containing non–natural amino acids.

Lam et al., 1991, 12th Amer. Pep. Symp., Abstract LW3 Rapid selection and structure determination of acceptor binding ligands from a large synthetic peptide library.

Lam et al., 1991, *Nature* 354:82–84 A new type of synthetic peptide library for identifying ligand–binding activity.

Mathur et al., 1980, *Polmyers as Aids in Organic Chemistry*, Academic Press, New York, Ch. 9–12:138–197.

Needels et al., 1993, *Proc. Natl. Acad. Sci. USA*, 90:10700–10704 Generation and screening of an oligonucleotide–encoded sythetic peptide library.

Nikolaiev et al., 1993, *Peptide Research*, 6(3):161–170 Peptide–encoding for structure determination of nonsequenceable polymers within libraries synthesized and tested on solid phase supports.

Ohlmeyer et al., 1993, *Proc. Natl. Acad. Sci. USA*, 90:10922–10926 Complex synthetic chemical libraries indexed with molecular tags.

Tjoeng et al., 1990, *Int. J. Pept. Protein Res.* 35:141–146 Multiple peptide synthesis using a single support (MPS3).

Van der Zee et al., 1989, *Eur. J. Immunol.* 19:43–48 Efficient mapping and characterization of a T cell epitope by the simultaneous synthesis of multiple peptides.

METHOD OF SYNTHESIZING DIVERSE COLLECTIONS OF OLIGOMERS

CROSS-REFERENCE

This application is a continuation of U.S. patent application Ser. No. 08/473,676 filed Jun. 6, 1995, now abandoned, which is a division of U.S. application Ser. No. 07/946,239 filed Sep. 16, 1992, now U.S. Pat. No. 5,770,358, which is a continuation-in-part of U.S. patent application Ser. No. 07/762,522, filed Sep. 18, 1991 now abandoned, each of which is incorporated herein by reference.

FIELD OF THE INVENTION

The present invention relates generally to stochastic methods for synthesizing random oligomers, with particular emphasis on particle-based synthesis methods. The invention also relates to the use of identification tags on the particles to facilitate identification of the oligomer sequence synthesized. Yet another aspect of the invention relates to the use of tagged oligomer libraries in receptor-binding studies.

BACKGROUND OF THE INVENTION

The relationship between structure and activity of molecules is a fundamental issue in the study of biological systems. Structure-activity relationships are important in understanding, for example, the function of enzymes, the ways in which cells communicate with each other, and cellular control and feedback systems. Certain macromolecules are known to interact and bind to other molecules having a very specific three-dimensional spatial and electronic distribution. Any large molecule having such specificity can be considered a receptor, whether the molecule is an enzyme catalyzing hydrolysis of a metabolic intermediate, a cell-surface protein mediating membrane transport of ions, a glycoprotein serving to identify a particular cell to its neighbors, an IgG-class antibody circulating in the plasma, an oligonucleotide sequence of DNA in the genome, or the like. The various molecules that receptors selectively bind are known as ligands.

Many assays are available for measuring the binding affinity of known receptors and ligands, but the information that can be gained from such experiments is often limited by the number and type of available ligands. Novel ligands are sometimes discovered by chance or by application of new techniques for the elucidation of molecular structure, including x-ray crystallographic analysis and recombinant genetic techniques for proteins.

Small peptides are an exemplary system for exploring the relationship between structure and function in biology. A peptide is a polymer composed of amino acid monomers. When the twenty naturally occurring amino acids are condensed into polymeric molecules, the resulting polymers form a wide variety of three-dimensional configurations, each resulting from a particular amino acid sequence and solvent condition. The number of possible pentapeptides of the 20 naturally occurring amino acids, for example, is $20^5$ or 3.2 million different peptides. The likelihood that molecules of this size might be useful in receptor-binding studies is supported by epitope analysis studies showing that some antibodies recognize sequences as short as a few amino acids with high specificity. Furthermore, the average molecular weight of amino acids puts small peptides in the size range of many currently useful pharmaceutical products. Of course, larger peptides may be necessary for many purposes, and polypeptides having changes in only a small number of residues may also be useful for such purposes as the analysis of structure-activity relationships.

Pharmaceutical drug discovery is one type of research that relies on studies of structure-activity relationships. In most cases, contemporary pharmaceutical research can be described as the process of discovering novel ligands with desirable patterns of specificity for biologically important receptors. Another example is research to discover new compounds for use in agriculture, such as pesticides and herbicides.

Prior methods of preparing large numbers of different oligomers have been painstakingly slow when used at a scale sufficient to permit effective rational or random screening. For example, the "Merrifield" method (Merrifield, *J. Am. Chem. Soc.* 85:2149–2154 (1963), which is incorporated herein by reference) has been used to synthesize peptides on a solid support. In the Merrifield method, an amino acid is covalently bonded to a support made of an insoluble polymer. Another amino acid with an alpha protected group is reacted with the covalently bonded amino acid to form a dipeptide. The protective group is removed, and a third amino acid with an alpha protective group is added to the dipeptide. This process is continued until a peptide of a desired length and sequence is obtained. Using the Merrifield method, one cannot economically and practically synthesize more than a few peptide sequences in a day.

To synthesize larger numbers of oligomer sequences, others have proposed the use of a series of reaction vessels for oligomer synthesis. For example, a tubular reactor system may be used to synthesize a linear oligomer on a solid phase support by automated sequential addition of reagents. This method still does not enable the synthesis of a sufficiently large number of oligomer sequences for effective economical screening.

Methods of preparing a plurality of oligomer sequences are also known in which a foraminous container encloses a known quantity of reactive solid supports, the solid supports being larger in size than openings of the container. See U.S. Pat. No. 4,631,211, incorporated herein by reference. The containers may be selectively reacted with desired materials to synthesize desired sequences of product molecules. As with other methods known in the art, this method cannot practically be used to synthesize a sufficient variety of polypeptides for effective screening.

Other techniques have also been described. One bead-based method is described in PCT patent publication No. 92/00091, incorporated herein by reference. These methods include the synthesis of peptides on 96 plastic pins that fit the format of standard microtiter plates. See PCT patent publications 84/03564; 86/00991; and 86/06487, each of which is incorporated herein by reference. Unfortunately, while these techniques have been somewhat useful, substantial problems remain. For example, these methods continue to be limited in the diversity of sequences which can be economically synthesized and screened.

Others have developed recombinant methods for preparing collections of oligomers. See PCT patent publication Nos. 91/17271 and 91/19818, each of which is incorporated herein by reference. In another important development, scientists combined the techniques of photolithography, chemistry, and biology to create large collections of oligomers and other compounds on the surface of a substrate. See U.S. Pat. No. 5,143,854 and PCT patent publication Nos. 90/15070 and 92/10092, each of which is incorporated herin by reference.

In the recombinant and VLSIPS™ combinatorial methods, one can uniquely identify each oligomer in the library by determining the coding sequences in the recombinant organism or phage or by the location of the oligomer on the VLSIPS™ chip. In other methods, however, the identity of a particular oligomer may be difficult to ascertain. What is needed in these latter methods is an efficient and simple-to-use method for tagging each particle. Although tagging methods have been developed for large objects, see PCT patent publication Nos. 90/14441 and 87/06383, each of which is incorporated herein by reference, such methods are still needed for combinatorial libraries of oligomers.

From the above, one can recognize that improved methods and apparatus for synthesizing a diverse collection of chemical sequences would be beneficial.

SUMMARY OF THE INVENTION

The present invention provides a general stochastic method for synthesizing libraries of random oligomers. The random oligomers are synthesized on solid supports, or particles, but may be cleaved from these supports to provide a soluble library. The oligomers are composed of a sequence of monomers, the monomers being any member of the set of molecules that can be joined together to form an oligomer or polymer, i.e., amino acids, carbamates, sulfones, sulfoxides, nucleosides, carbohydrates, ureas, phosphonates, lipids, esters, combinations of the same, and the like. The library is then screened to isolate individual oligomers that bind to a receptor or possess some desired property. Each oligomer sequence in the library is unique, in a preferred embodiment. In another preferred embodiment, the solid supports are nonporous beads. The solid supports may be composed of a single particle, or two or more linked particles.

A further embodiment of the invention relates to the use of an identifier tag to identify the sequence of monomers in the oligomer. The identifier tag, which may be attached directly to the oligomer with or without an accompanying particle, to a linker attached to the oligomer, to the solid support upon which the oligomer is synthesized, or to a second particle attached to the oligomer-carrying particle, may be any recognizable feature that in some way carries the required information, and that is decipherable at the level of one or a few solid supports. The solid supports may be joined to the oligomers and the identifier tag by means of one or more linker molecules.

In a preferred embodiment, the identifier tag will be an oligonucleotide, preferably composed of pyrimidines or pyrimidines and purine analogs or any type of nucleoside that will not degrade under the coupling conditions used to assemble the oligomer library. The oligonucleotide identifier tag may contain a 5' and a 3' amplification site, to allow amplification of the tag by, for example, the polymerase chain reaction (see U.S. Pat. Nos. 4,683,202; and 4,965,188, each of which is incorporated herein by reference). A DNA sequencing primer site, which may be specific for each step of the oligomer synthesis, may also be included in the oligonucleotide tag in addition to the amplification primer sites. The tag may be designed to include, in the oligonucleotide sequence, information allowing identification of the monomer associated with the addition of the particular tag. The oligonucleotide tag will be about 50 to 100 nucleotides in length, in a preferred embodiment.

In another preferred embodiment, the identifier tag may be composed of a set of light-addressable compounds, such as fluorescent or phosphorescent compounds that can be photobleached, which compounds are incorporated into the beads or particles on which the oligomers of the oligomer library are synthesized. Such compounds are widely known in the art.

DESCRIPTION OF THE SPECIFIC EMBODIMENTS

Figure 1:
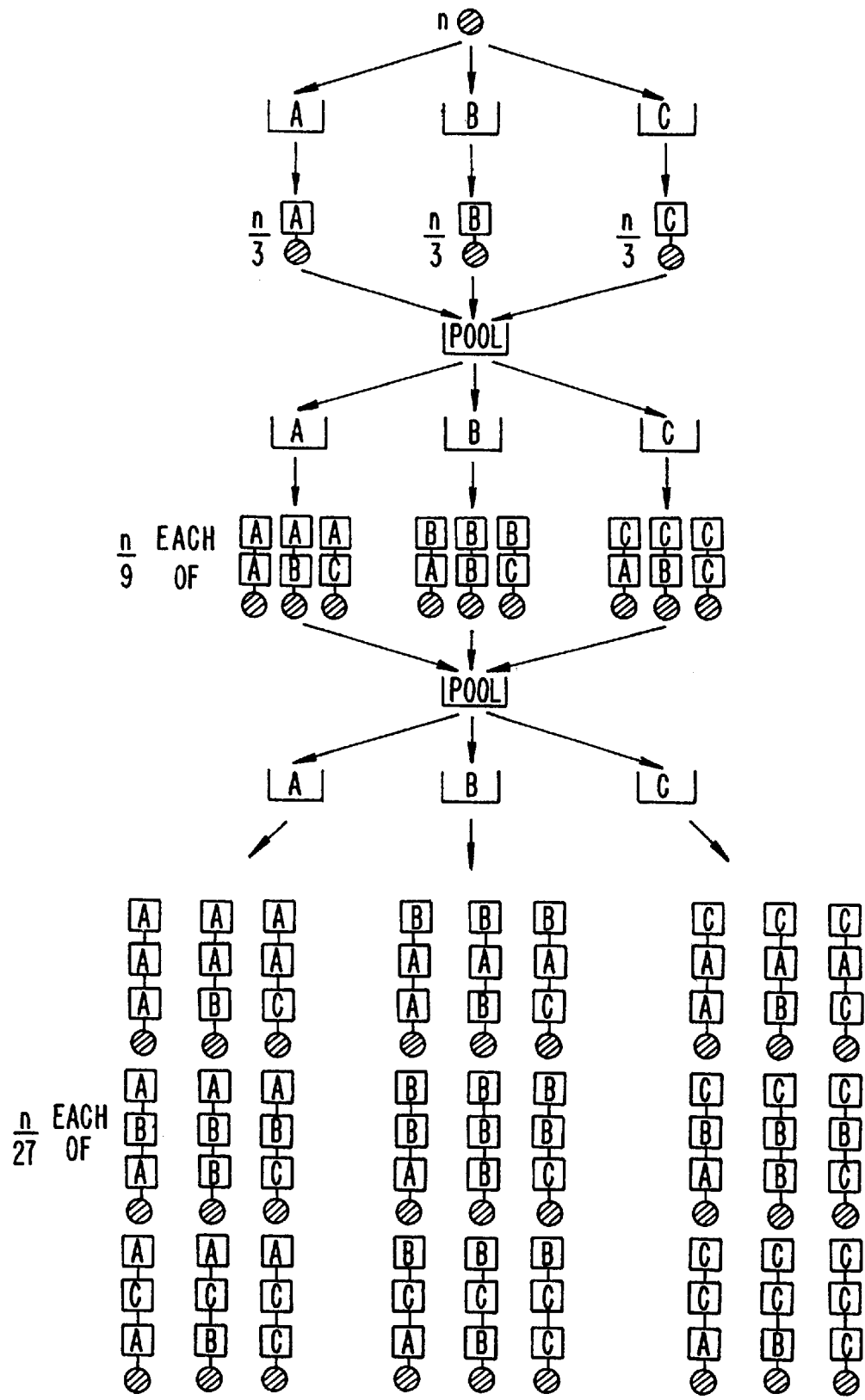
FIG. 1 is a schematic representation of combinatorial oligomer synthesis on particles.

The present invention provides novel methods and instruments for producing large synthetic oligomer libraries. In a preferred embodiment of the present invention, each member of such a library is uniquely labeled in a manner that specifies the identity of the sequence of the oligomer corresponding to that member. Methods for screening such libraries and reagents useful for producing the libraries are also provided.

Glossary

The following terms are intended to have the following general meanings as they are used herein:

Complementary or substantially complementary: These terms refer to base pairing between nucleotides or nucleic acids, such as, for instance, between the two strands of a double stranded DNA molecule or between an oligonucleotide primer and a primer binding site on a single stranded nucleic acid to be sequenced or amplified. "Complementary" nucleotides are, generally, A and T (or A and U), and C and G, as is well known to those of skill in the art. Two single stranded RNA or DNA molecules are said to be "substantially complementary" when the nucleotides of one strand, optimally aligned, pair with at least about 80% or more of the nucleotides of the other strand.

Alternatively, substantial complementarity exists when an RNA or DNA strand will hybridize under selective hybridization conditions to a complementary nucleic acid. Typically, selective hybridization will occur when there is at least about 55% complementarity over a stretch of at least 14 to 25 nucleotides, but more selective hybridization will occur as complementarity increases to 65%, 75%, 90%, and 100%. See Kanehisa, *Nucleic Acids Res.* 12:203 (1984), incorporated herein by reference.

Stringent hybridization conditions will typically include salt concentrations of less than about 1 M, such as less than 500 mM, and will often include salt concentrations of less than 200 mM. The hybridization temperature for oligomers will typically be greater than 22° C., such as greater than about 30° C., and will often be in excess of about 37° C. Longer fragments may require higher hybridization temperatures for specific hybridization. As other factors may dramatically affect the stringency of hybridization (such factors include base composition, length of the complementary strands, presence of organic solvents, and extent of base mismatching), the combination of factors is more important than the absolute measure of any one factor alone.

Epitope: The portion of an antigen molecule delineated by the area of interaction with the subclass of receptors known as antibodies is an "epitope."

Identifier tag: An "identifier tag" is a physical attribute that provides a means whereby one can identify which monomer reactions an individual solid support has experienced in the synthesis of an oligomer. The identifier tag also records the step in the synthesis series in which the solid support visited that monomer reaction. The identifier tag may be any recognizable feature, including for example: a microscopically distinguishable shape, size, color, optical density, etc.; a differential absorbance or emission of light; chemically reactivity; magnetic or electronic encoded information; or any other distinctive mark with the required information, and decipherable at the level of one (or a few) solid support(s). A preferred example of such an identifier tag is an oligonucleotide sequence. An "identifier tag" can be coupled directly to the oligomer synthesized, whether or not a solid support is used in the synthesis. In this latter embodiment, the identifier tag serves as the "support" for oligomer synthesis.

Ligand: A "ligand" is a molecule that is recognized by a particular receptor. The agent bound by or reacting with a receptor is called a "ligand", a term which is definitionally meaningful only in terms of its counterpart receptor. The term "ligand" does not imply any particular molecular size or other structural or compositional feature other than that the substance in question is capable of binding or otherwise interacting with the receptor. Also, a "ligand" may serve either as the natural ligand to which the receptor binds, or as a functional analogue that may act as an agonist or antagonist. Ligands that can be investigated by this invention include, but are not restricted to, agonists and antagonists for cell membrane receptors, toxins and venoms, viral epitopes, hormones, sugars, cofactors, peptides, enzyme substrates, cofactors, drugs (e.g., opiates, steroids, etc.), and proteins.

Monomer: A "monomer" is any member of the set of molecules which can be joined together to form an oligomer or polymer. The set of monomers useful in the present invention includes, but is not restricted to, for the example of peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer.

Oligomer or Polymer: The "oligomer" or "polymer" sequences of the present invention are formed from the chemical or enzymatic addition of monomer subunits. Such oligomers include, for example, both linear, cyclic, and branched polymers of nucleic acids, polysaccharides, phospholipids, and peptides having either alpha-, beta-, or omega-amino acids, heteropolymers, polyurethanes, polyesters, polycarbonates, polyureas, polyamides, polyethyleneimines, polyarylene sulfides, polysiloxanes, polyimides, polyacetates, or other polymers, as will be readily apparent to one skilled in the art upon review of this disclosure.

Peptide: A "peptide" is an oligomer in which the monomers are alpha amino acids joined together through amide bonds. Alternatively, a "peptide" can be referred to as a "polypeptide." In the context of this specification, one should appreciate that the amino acids may be the L-optical isomer or the D-optical isomer. Peptides are more than two amino acid monomers long, but more often are more than 5 to 10 amino acid monomers long and can be even longer than 20 amino acids, although peptides longer than 20 amino acids are more likely to be called "polypeptides." Standard single letter abbreviations for amino acids are used (e.g., P for proline). These abbreviations are included in Stryer, *Biochemistry*, Third Ed. (1988), which is incorporated herein by reference.

Oligonucleotides: An "oligonucleotide" is a single-stranded DNA or RNA molecule, typically prepared by synthetic means. Those oligonucleotides employed in the present invention will usually be 50 to 150 nucleotides in length, preferably from 80 to 120 nucleotides, although oligonucleotides of different length may be appropriate in some circumstances. For instance, in one embodiment of the invention, the oligonucleotide tag and the polymer identified by that tag are synthesized in parallel. In this embodiment, the oligonucleotide tag can be built nucleotide-bynucleotide in coordination with the monomer-by-monomer addition steps used to synthesize the oligomer. In addition, very short, i.e., 2 to 10 nucleotides, oligonucleotides may be used to extend an existing oligonucleotide tag to identify a monomer coupling step. Suitable oligonucleotides may be prepared by the phosphoramidite method described by Beaucage and Carruthers, *Tetr. Lett.* 22:1859–1862 (1981), or by the triester method, according to Matteucci et al., *J. Am. Chem. Soc.* 103:3185 (1981), both incorporated herein by reference, or by other methods such as by using commercial automated oligonucleotide synthesizers.

Operably linked: A nucleic add is "operably linked" when placed into a functional relationship with another nucleic acid sequence. For instance, a promoter or enhancer is "operably linked" to a coding sequence if the promoter causes the transcription of the sequence. Generally, operably linked means that the DNA sequences being linked are contiguous and, where necessary to join two protein coding regions, contiguous and in reading frame.

Receptor: A "receptor" is a molecule that has an affinity for a given ligand. Receptors may be naturally-occurring or manmade molecules. Also, receptors can be employed in their unaltered natural or isolated state or as aggregates with other species. Receptors may be attached, covalently or noncovalently, to a binding member, either directly or via a specific binding substance. Examples of receptors that can be employed in the method of the present invention include, but are not restricted to, antibodies, cell membrane receptors, monoclonal antibodies, antisera reactive with specific antigenic determinants (such as on viruses, cells, or other materials), polynucleotides, nucleic acids, lectins, polysaccharides, cells, cellular membranes, and organelles. Receptors are sometimes referred to in the art as "antiligands." As the term "receptor" is used herein, no difference in meaning is intended. A "ligand-receptor pair" is formed when two macromolecules have combined through molecular recognition to form a complex.

Other examples of receptors that can be investigated by this invention include, but are not restricted to:

Microorganism receptors: Determination of ligands that bind to microorganism receptors, such as specific transport proteins or enzymes essential to survival of microorganisms, is useful in discovering new classes or types of antibiotics. Of particular value would be antibiotics against opportunistic fungi, protozoa, and those bacteria resistant to the antibiotics in current use.

Enzymes: For instance, the binding site of any enzyme, such as the enzymes responsible for cleaving neurotransmitters, is a receptor. Determination of ligands that bind to certain enzymes, and thus modulate the action of the enzymes that cleave the different neurotransmitters, is useful in the development of drugs that can be used in the treatment of disorders of neurotransmission.

Antibodies: For instance, the invention may be useful in investigating the ligand-binding site on an antibody molecule that combines with the epitope of an antigen of interest. Determining a sequence that mimics an antigenic epitope may lead to the development of vaccines or lead to the development of related diagnostic agents or compounds useful in therapeutic treatments such as for autoimmune diseases (e.g., by blocking the binding of the "self" antibodies).

Nucleic Acids: The invention may be useful in investigating sequences of nucleic acids acting as binding sites for cellular proteins ("trans-acting factors"). Such sequences may include, e.g., enhancers or promoter sequences.

Catalytic Polypeptides: Polymers, preferably polypeptides, which are capable of promoting a chemical reaction involving the conversion of one or more reactants to one or more products are "catalytic polypeptides." Such polypeptides generally include a binding site specific for at least one reactant or reaction intermediate and an active functionality proximate to the binding site, which functionality is capable of chemically modifying the bound reactant. Catalytic polypeptides are described in, Lerner et al., *Science* 252: 659 (1991), which is incorporated herein by reference.

Hormone receptors: For instance, "hormone receptors" include the receptors for insulin and growth hormone. Determination of the ligands which bind with high affinity to a hormone receptor is useful in the development of, for example, an oral replacement of the daily injections which diabetics must take to relieve the symptoms of diabetes, and in the other case, a replacement for human growth hormone, which can only be obtained from cadavers or by recombinant DNA technology. Other examples include the vasoconstrictive hormone receptors; determination of ligands that bind to those receptors may lead to the development of drugs to control blood pressure.

Opiate receptors: Determination of ligands that bind to the opiate receptors in the brain is useful in the development of less-addictive replacements for morphine and related drugs.

Substrate or Solid Support: A "substrate or solid support" is a material having a rigid or semi-rigid surface. Such materials will preferably take the form of small beads, pellets, disks, or other convenient forms, although other forms may be used. In some embodiments, at least one surface of the substrate will be substantially flat. A roughly spherical shape is preferred.

Synthetic: A compound is "synthetic" when produced by in vitro chemical or enzymatic synthesis. The synthetic libraries of the present invention may be contrasted with those in viral or plasmid vectors, for instance, which may be propagated in bacterial, yeast, or other living hosts.

I. Method for Producing Large Synthetic Oligomer Libraries

A general method of random oligomer synthesis is provided by the present invention. The method can be used to produce the enormous numbers of compounds available with recombinant systems and to utilize the monomer set diversity available with chemical synthesis methods. By means of the present method, one can readily produce up to $10^{12}$ different oligomers, a dramatic improvement over previous methods. The invention also provides a facile means of oligomer identification.

The general method comprises producing a large, highly diverse collection or library, each member of such a library comprising a single oligomer sequence (e.g., a peptide). The sequence may be soluble or may be bound to a solid support. When bound to a solid support, the oligomer is usually attached by means of a linker. The linker, prior to attachment, has an appropriate functional group at each end, one group appropriate for attachment to the support and the other group appropriate for attachment to the oligomer. Such a collection may contain, for example, all combinations of n monomers assembled into X length oligomers yielding, $n^X$ different compounds. The collection may also contain oligomers having different monomer units at, for example, only one or a small number of positions, while having an identical sequence at all other positions. The general method typically involves synthesizing the oligomers in a random combinatorial ("stochastic") fashion by chemical and/or enzymatic assembly of monomer units.

A synthetic oligomer library may be produced by synthesizing on each of a plurality of solid supports a single oligomer sequence, the oligomer sequence being different for different solid supports. The oligomer sequence is synthesized in a process comprising the steps of: (a) apportioning the supports in a stochastic manner among a plurality of reaction vessels; (b) exposing the supports in each reaction vessel to a first monomer; (c) pooling the supports; (d) apportioning the supports in a stochastic manner among the plurality of reaction vessels; (e) exposing the supports in each reaction vessel to a second monomer; and (f) repeating steps (a) through (e) from at least one to twenty times. Typically, substantially equal numbers of solid supports will be apportioned to each reaction vessel. In one embodiment of the method, the monomers are chosen from the set of amino acids, and the resulting oligomer is a peptide.

As a specific example of the method, one may consider the synthesis of peptides three residues in length, assembled from a monomer set of three different monomers: A, B, and C. The first monomer is coupled to three different aliquots of beads, each different monomer in a different aliquot, and the beads from all the reactions are then pooled (see FIG. 1). The pool now contains approximately equal numbers of three different types solid supports, with each type characterized by the monomer in the first residue position. The pool is mixed and redistributed to the separate monomer reaction tubes or vessels containing A, B, or C as the monomer. The second residue is coupled.

Following this reaction, each tube now has beads with three different monomers in position one and the monomer contained in each particular second reaction tube in position 2. All reactions are pooled again, producing a mixture of beads each bearing one of the nine possible dimers. The pool is again distributed among the three reaction vessels, coupled, and pooled. This process of sequential synthesis and mixing yields beads that have passed through all the possible reaction pathways, and the collection of beads displays all trimers of three amino acids ($3^3=27$). Thus, a complete set of the trimers of A, B, and C is constructed. As can be readily appreciated, the use of a sufficiently large number of synthesis beads helps to ensure that the set completely represents the various combinations of monomers employed in this random, combinatorial synthesis scheme.

This method of assembling oligomers from many types of monomers requires using the appropriate coupling chemistry for a given set of monomer units or building blocks. Any set of building blocks that can be attached to one another in a step-by-step fashion can serve as the monomer set. The attachment may be mediated by chemical, enzymatic, or other means, or by a combination of any of these means. The resulting oligomers can be linear, cyclic, branched, or assume various other conformations as will be apparent to those skilled in the art. Techniques for solid state synthesis of polypeptides are described, for example, in Merrifield, supra. Peptide coupling chemistry is also described in *The Peptides,* Vol. 1 (eds. Gross, E., and J. Meienhofer, Academic Press, Orlando (1979)), which is incorporated herein by reference.

To synthesize the oligomers, a collection of a large number of the solid supports is apportioned among a number of reaction vessels. In each reaction, a different monomer is coupled to the growing oligomer chain. The monomers may be of any type that can be appropriately activated for chemical coupling or accepted for enzymatic coupling. Because the reactions may be contained in separate reaction vessels, even monomers with different coupling chemistries can be used to assemble the oligomers (see *The Peptides,* supra). The coupling time for some of the monomer sets may be long. For this reason, the preferred arrangement is one in which the monomer reactions are carried out in parallel. After each coupling step, the solid supports on which are synthesized the oligomers of the library are pooled and mixed prior to re-allocation to the individual vessels for the next coupling step. This shuffling process produces solid supports with many oligomer sequence combinations. If each synthesis step has high coupling efficiency, then substantially all the oligomers on a single solid support have the same sequence. That sequence is determined by the synthesis pathway (type and sequence of monomer reactions) for any given solid support at the end of the synthesis. The maximum length of the oligomers is typically less than about 20, usually from 3 to 8 residues in length, but in some cases a length of 10 to 12 residues is preferred. Protective groups known to those skilled in the art may be used to prevent spurious coupling (see *The Peptides,* Vol. 3 (eds. Gross, E., and J. Meienhofer, Academic Press, Orlando (1981), which is incorporated herein by reference).

Modifications of this completely random approach are also possible. For example, the monomer set may be expanded or contracted from step to step; or the monomer set could be changed completely for the next step (e.g., amino acids in one step, nucleosides in another step, carbohydrates in another step), if the coupling chemistry were available (see Gait, *Oligonucleotide Synthesis: A Practical Approach,* IRL Press, Oxford (1984); Friesen and Danishefsky, *J. Amer. Chem. Soc.* 111:6656 (1989); and Paulsen, *Angew. Chem. Int. Ed. Engl.* 25:212 (1986), all of which are incorporated herein by reference). A monomer unit for peptide synthesis, for example, may include single amino acids or larger peptide units, or both. One variation is to form several pools of various sequences on solid supports to be distributed among different monomer sets at certain steps of the synthesis. By this approach, one can also build oligomers of different lengths with either related or unrelated sequences, and one can fix certain monomer residues at some positions while varying the other residues, to construct oligomer frameworks wherein certain residues or regions are altered to provide diversity.

The chemical or enzymatic synthesis of the oligomer libraries of the present invention typically takes place on solid supports. The term "solid support" as used herein embraces a particle with appropriate sites for oligomer synthesis and, in some embodiments, tag attachment and/or synthesis. There are various solid supports useful in preparation of the synthetic oligomer libraries of the present invention. Solid supports are commonly used for solid phase synthesis of, for example, peptides and nucleic acids and other oligomers as enumerated above, and thus are well known to those skilled in the art.

With enough solid supports and efficient coupling, one can generate complete sets of certain oligomers, if desired. In general, the solid support size is in the range of 1 nm to 100 $\mu$m, but a more massive solid support of up to 1 mm in size may be used. The appropriate size of the solid support depends on (1) the number of oligomer synthesis sites and identifier tag attachment sites desired; (2) the number of different compounds to be synthesized (and the number of solid supports bearing each oligomer that are needed for screening); and (3) the effect of the size of the solid supports on the specific screening strategies [e.g., fluorescence-activated cell sorters (FACS)] to be used.

As a specific example, solid supports of 1 $\mu$m in diameter may be used. If each reaction contains approximately 0.2 mL of solid supports, and the oligomers are synthesized from a set of 50 monomers (50 parallel reactions), then a total of 10 mL of solid supports, or approximately $10^{13}$ solid supports, would be required. If one wishes to make hexamers with these 50 monomers, then there are over $1.5 \times 10^{10}$ possible sequences, and each specific sequence would be represented on about $10^3$ solid supports. An estimated capacity of each bead, based on the capacity of commonly used peptide synthesizing resins, is about 0.1 pg of peptide per bead. By this estimation, then, each solid support would have about 100 amol or $10^8$ oligomer chains.

To improve washing efficiencies, solid supports less porous than typical peptide synthesis resins are preferable. These supports will have a lower density of growing chains, but even with a decrease in capacity of several orders of magnitude, sufficient oligomer densities can be produced for efficient screening. With the less porous supports, a greater proportion of the oligomers will be accessible for binding to the receptor during the screening process. Also, the less porous supports will reduce the carryover of tags from one reaction to the next, thus improving the accuracy of reading the dominant (correct) tags.

Such solid supports may be of any shape, although they will preferably be roughly spherical. The supports need not necessarily be homogenous in size, shape, or composition; although the supports usually and preferably will be uniform. In some embodiments, supports that are very uniform in size may be particularly preferred. In another embodiment, however, two or more distinctly different populations of solid supports may be used for certain purposes.

Solid supports may consist of many materials, limited primarily by capacity for derivatization to attach any of a number of chemically reactive groups and compatibility with the chemistry of oligomer synthesis and tag attachment. Suitable support materials include glass, latex, heavily cross-linked polystyrene or similar polymers, gold or other colloidal metal particles, and other materials known to those skilled in the art. Except as otherwise noted, the chemically reactive groups with which such solid supports may be derivatized are those commonly used for solid state synthesis of the respective oligomer and thus will be well known to those skilled in the art. The solid supports of the present invention do not include living cells, viruses, or cloning vectors such as phage vectors or plasmids.

II. Method for Producing Tagged Synthetic Oligomer Libraries

In a preferred embodiment of the invention, the oligomers comprising the library also are attached to an identifier tag that can be easily decoded to report the sequence of each oligomer. The identifier tags may be attached either to the oligomer or to the solid support to which the oligomer is attached. The attachment is preferably by means of a linker that, prior to attachment, has an appropriate functional group at each end, one group appropriate for attachment to the support and the other group appropriate for attachment to the identifier tag. Alternatively, the identifier tag may be attached to a monomer incorporated into the oligomer or attached directly to the same linker that binds the oligomer to the solid support. In the latter embodiment, the linker has, prior to attachment, a third functional group appropriate for the attachment of the identifier tag.

A synthetic oligomer library that incorporates identifier tags is produced by synthesizing on each of a plurality of solid supports a single oligomer sequence and one or more identifier tags identifying the oligomer sequence. The tagged synthetic oligomer library is synthesized in a process comprising the steps of: (a) apportioning the supports among a plurality of reaction vessels; (b) exposing the supports in each reaction vessel to a first oligomer monomer and to a first identifier tag monomer; (c) pooling the supports; (d) apportioning the supports among a plurality of reaction vessels; and (e) exposing the supports to a second oligomer monomer and to a second identifier tag monomer. As noted above, one can also practice the invention in a mode in which there is no solid support; in this mode, the tag is attached directly to the oligomer being synthesized. The steps of either process typically will be repeated one or more times, but usually, will be repeated less than 20 times.

The solid supports can be exposed to (or coupled with) an oligomer monomer and an identifier tag at the same time, or sequentially. In either event, the supports are then pooled and exposed to the second oligomer monomer and second identifier tag. As before, these steps are repeated, typically from one to about 20 times. The invention is described herein primarily with regard to the preparation of molecules containing sequences of amino acids, but the invention can readily be applied to the preparation of other oligomers and to any set of compounds that can be synthesized in a component-by-component fashion, as can be appreciated by those skilled in the art.

In another embodiment, the same solid support is used for synthesizing all members of the library, but the members are cleaved from the support prior to screening. In this embodiment, synthesis of tagged oligomers may be accomplished utilizing very large scale immobilized polymer synthesis (VLSIPS™) techniques. See U.S. Pat. No. 5,143,854 and PCT patent publication No. 92/10092, each of which is incorporated herein by reference. An array of oligonucleotides is synthesized on the VLSIPS™ chip, each oligonucleotide linked to the chip by a cleavable group such as a disulfide. See U.S. patent application Ser. No. 874,849, filed Apr. 24, 1992, incorporated herein by reference. In one embodiment, each oligonucleotide tag has an amine group at the free end and only contains pyrimidine or pyrimidine and purine analog bases. In addition each oligonucleotide contains binding sites for amplification, i.e., PCR primer sites and optionally a sequencing primer site. A short section of each oligonucleotide uniquely codes the monomer sequence of the oligomer to be tagged. Then, e.g., peptides are synthesized, optionally from the free terminal amine groups on each oligonucleotide, so that each peptide is linked to a tag. The whole collection of oligonucleotide-peptide may be released from the chip to create a soluble tagged oligomer library.

More preferably, however, the oligomer library is constructed on beads or particles. One method of bead functionalization, with compatible chemistries for peptide synthesis and round by round attachment of oligonucleotide identifier tags, is shown in FIGS. 3.1–3.6. Glass beads are derivatized using aminopropyltriethoxysilane and a beta-alanine spacer group is coupled using activated ester methodology. The oligonucleotide tags may optionally incorporate a biotin group to facilitate purification, hybridization, amplification, or detection (see *Pierce ImmunoTechnology Catalog and Handbook,* 1991, incorporated herein by reference). Commercially available Fmoc protected amino acids and standard BOP coupling chemistry is employed for peptide synthesis (see *The Peptides,* supra). Protected polypyrimidine (e.g., cytidine protected as $N^4$-Bz-C) and/or purine analog containing oligonucleotides resistant to the coupling and deprotection reagents used in peptide synthesis are attached using maleimide chemistry to unmasked thiol groups incorporated into growing peptide chains at low frequency (i.e., 0.1%) as cysteine residues with masked thiol groups (which masks may be selectively removed prior to tagging). In other embodiments of the invention, one may not need to use protected nucleosides or oligonucleotides.

However, to maintain the integrity of an oligonucleotide tag during peptide synthesis, one may need to use different combinations of protecting groups and/or synthetic nucleotides to avoid degradation of the tag or the oligomer synthesized. In general, polypyrimidine oligonucleotide tags are relatively stable under typical peptide synthesis conditions, as opposed to oligonucleotide tags that contain natural purine nucleotides, but a polypyrimidine nucleotide tag may be somewhat refractory to amplification by PCR. One may need to incorporate purine bases, or analogs tested for ability to withstand peptide coupling (and deprotection) conditions, into the tag to acheive a desired efficiency of amplification. For purposes of the present invention, the tag optionally may contain from 10 to 90%, more preferably 35 to 50%, and most preferably 33 to 35%, purine or purine analog nucleotides. The oligonucleotides optionally may contain phosphate protecting groups (e.g., O-methyl phosphates) with greater base stability than the standard beta-cyanoethyl group, which may be susceptible to piperidine cleavage. In such cases, peptide and oligonucleotide deprotection can be effected by sequential treatment with thiophenol, trifluoroacetic acid, and ethanolic ethylenediamine at 55 degrees C. In another embodiment, photolabile alpha-amino protecting groups are used in conjunction with base-labile side chain protecting groups for the amino acids, and standard beta-cyanoethyl protecting groups are used for the oligonucleotide tags.

In another embodiment, oligonucleotides containing both modified or synthetic purines and pyrimidines may be synthesized in parallel with peptides using conventional Fmoc/$^t$Bu protected amino acids. In this method, one can also use O-allyl and N-allyloxycarbonyl groups to provide protection for phosphate oxygens and the exocyclic amines of the nucleoside bases, respectively (see Hayakawa et al., *J. Amer. Chem. Soc.* 112: 1691–1696 (1990), incorporated herein by reference). By employing the mild oxidant $^t$BuOOH for oxidation at the phosphorous, one can minimize oxidation of the amino acids methionine, tryptophan, and histidine (see Hayakawa et al., *Tetr. Lett.* 27:4191–4194 (1986), incorporated herein by reference). Use of pyridinium hydrochloride/imidazole as a phosphporamidite activator leads to selective 5'-O-phosphitylation at the expense of low levels of spurious reaction at nitrogen on the peptide or oligonucleotide (see Gryaznov and Letsinger, *Nucleic Acids Research* 20: 1879–1882 (1992) incorporated herein by reference). The lability of purine nucleotides to strong acid (e.g., TFA) is avoided by use of phosphoramidites of the purine nucleoside analogs 7-deaza-2'-deoxyadenosine and 7-deaza-2'-deoxyguanosine (see Barr et al., *BioTechniques* 4:428–432 (1986), and Scheit, *Nucleotide Analogs: Synthesis and Biological Function* pp. 64–65 (John Wiley and Sons, New York), both incorporated herein by reference).

The fully assembled peptide and oligonucleotide chains may be deprotected by first treating the products with 30% piperidine in DMF to remove amino-terminal Fmoc groups. Then, the allylic protecting groups are removed using THF containing tris (dibenzylideneacetone) dipalladium-chloroform complex, triphenylphosphine, and n-butylamine/formic acid, followed by a THF wash, an aqueous sodium N,N-diethyldithiocarbamate wash, and a water wash. Finally, the acid-labile amino acid protecting groups are removed by treatment with 95:5 TFA/water.

Figure 5:
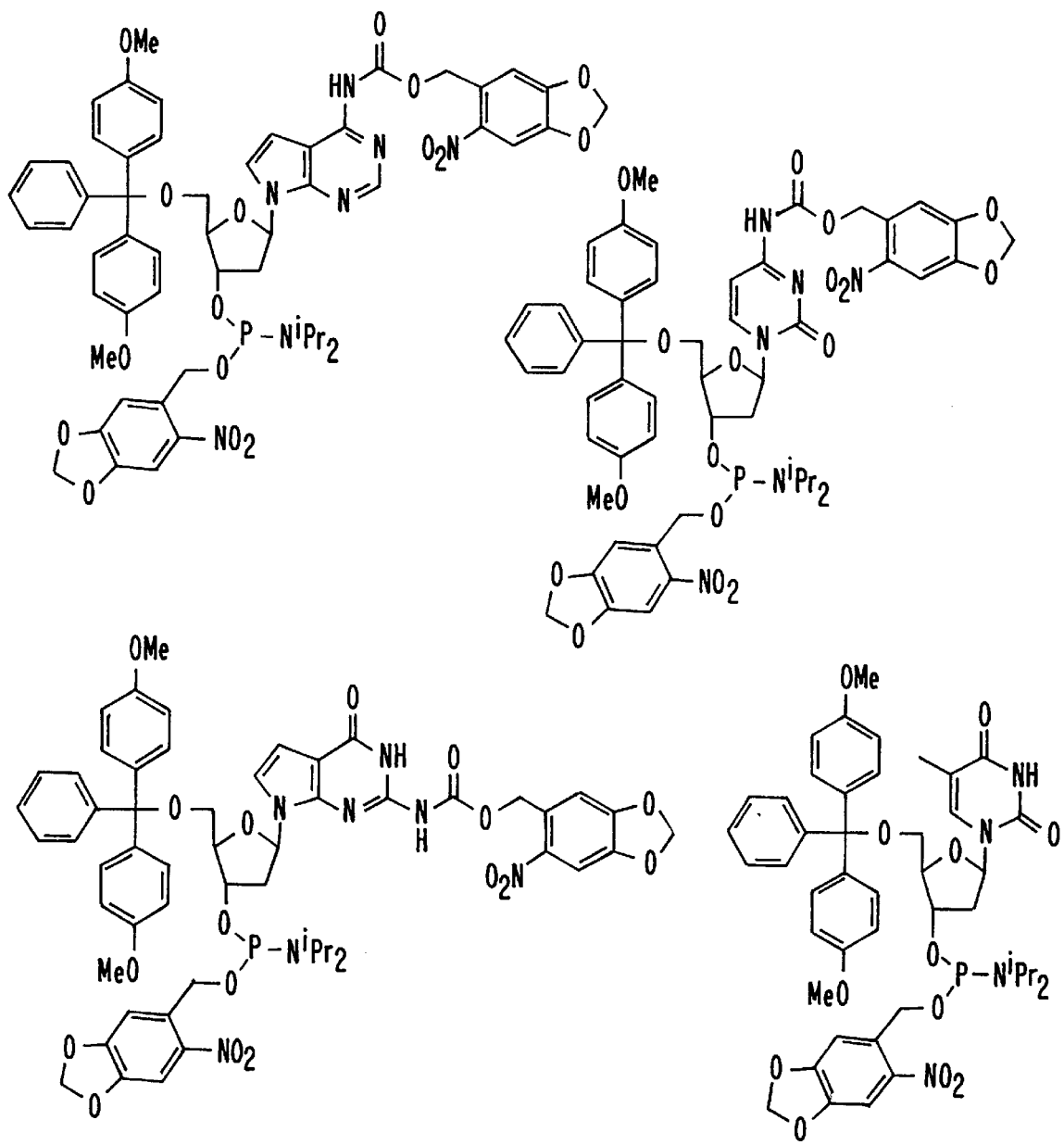
FIG. 5 illustrates nucleoside phosphoramidites derivatized with photolabile protecting groups for parallel peptide/oligonucleotide synthesis.

Other methods also provide effective orthogonal protection during the parallel assembly of oligonucleotides and peptides. These methods include use of acid-labile protecting groups on phosphates and exocyclic amines of deoxycytidine, 7-deaza-deoxyadenosine, and 7-deaza-deoxyguanosine sufficiently robust to resist the 3% trichloroacetic acid used in 5'-0-detritylation; use of photochemically removable protecting groups on these residues; and combinations of such acid and photolabile groups (for photolabile protecting groups for phosphate, see Baldwin et al., *Tetr. Lett.* 46: 6879–6884 (1990), incorporated herein by reference; see also FIG. 5).

III. Identifying the Sequence of any Oligomer

The present invention provides a method for identifying the composition and sequence of any of the oligomers in the library. By tracking the synthesis pathway that each oligomer has taken, one can deduce the sequence of monomers of any oligomer. The method involves linking an identifier tag to the oligomer that indicates the monomer reactions and corresponding step numbers that define each oligomer in the library. After a series of synthesis steps (and concurrent identifier tag additions), one "reads" the identifier tag(s) associated with an oligomer to determine the sequence of that oligomer.

Figure 2:
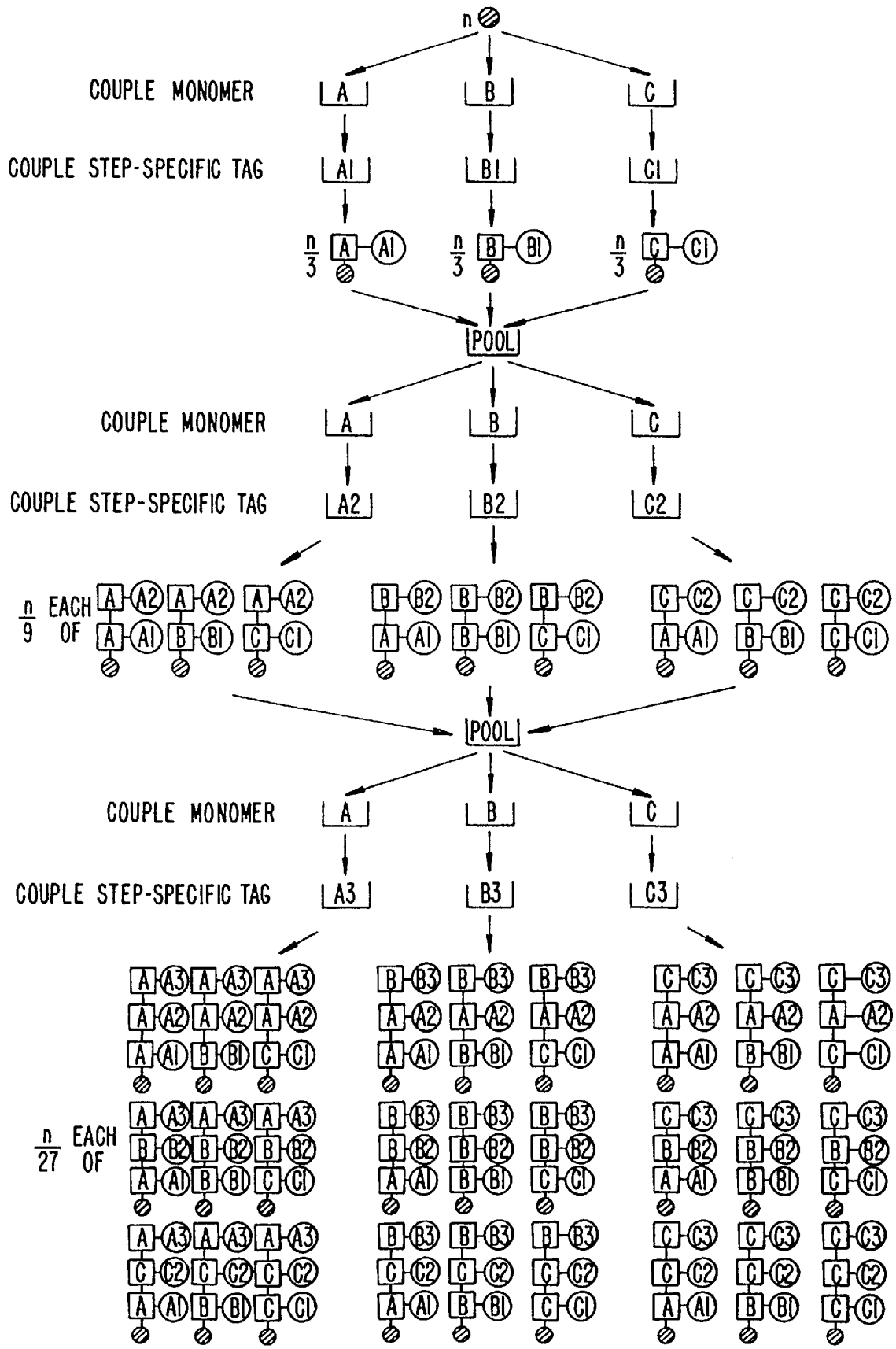
FIG. 2 is a schematic representation of concurrent combinatorial oligomer synthesis and particle tagging.
Figure 3A:
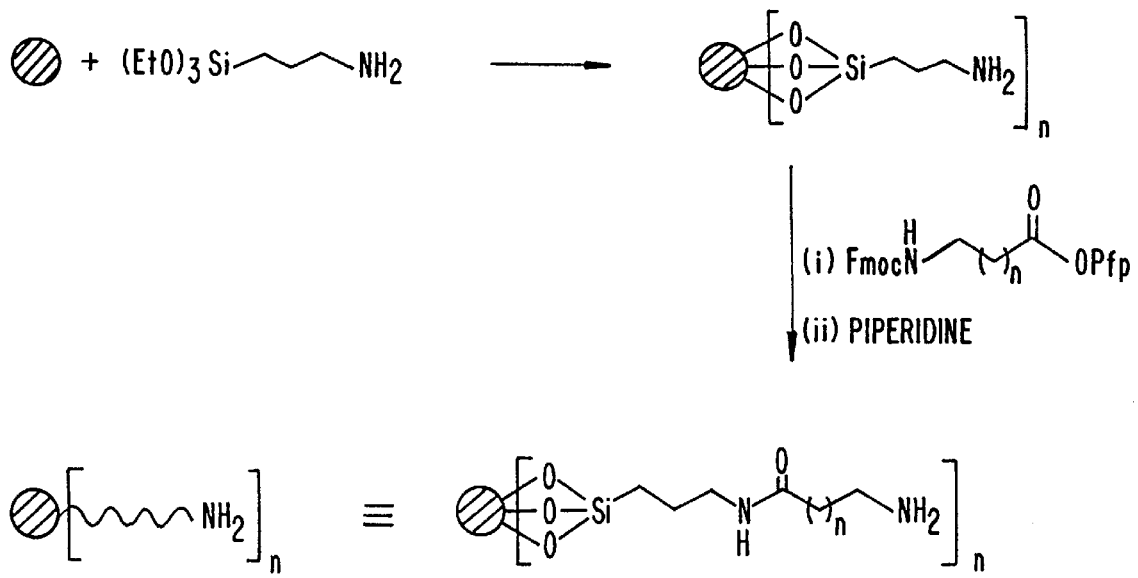
FIG. 3 describes one method of bead functionalization, the compatible chemistries for peptide synthesis and round by round attachment of oligonucleotide identifier tags, including synthesis of amino-functionalized beads, shown in FIG. 3A; the structure of protected 5' maleimidyl oligonucleotides, shown in FIG. 3B; amino acid coupling and introduction of a thiol "handle," shown in FIG. 3C; step-specific oligonucleotide attachment to a bead, shown in FIG. 3D; subsequent amino acid coupling(s) and oligonucleotide attachment(s), shown in FIG. 3E; and peptide and oligonucleotide deprotection, shown in FIG. 3F.
Figure 3B:
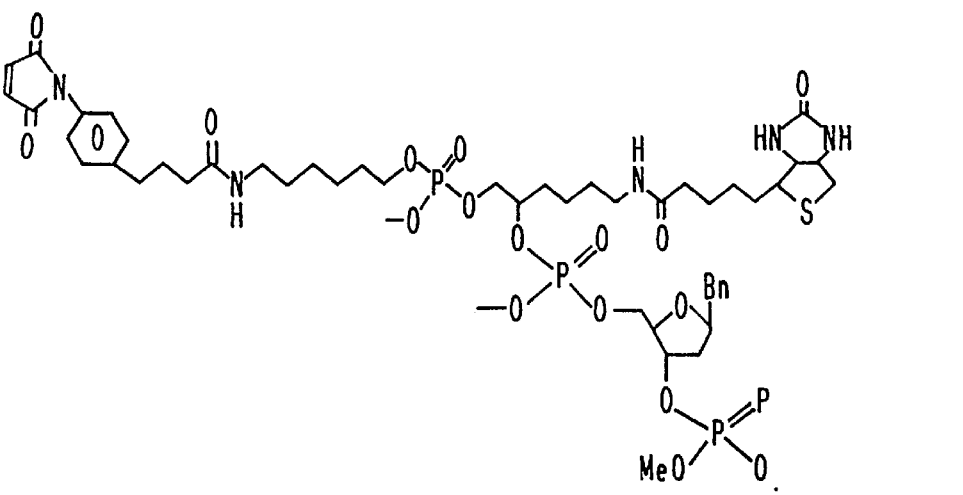
Figure 3B:
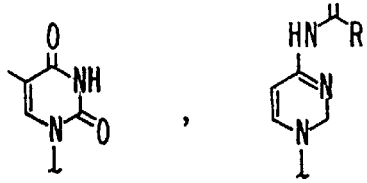
Figure 3B:
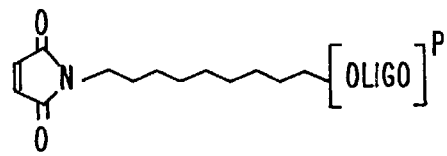
Figure 3C:
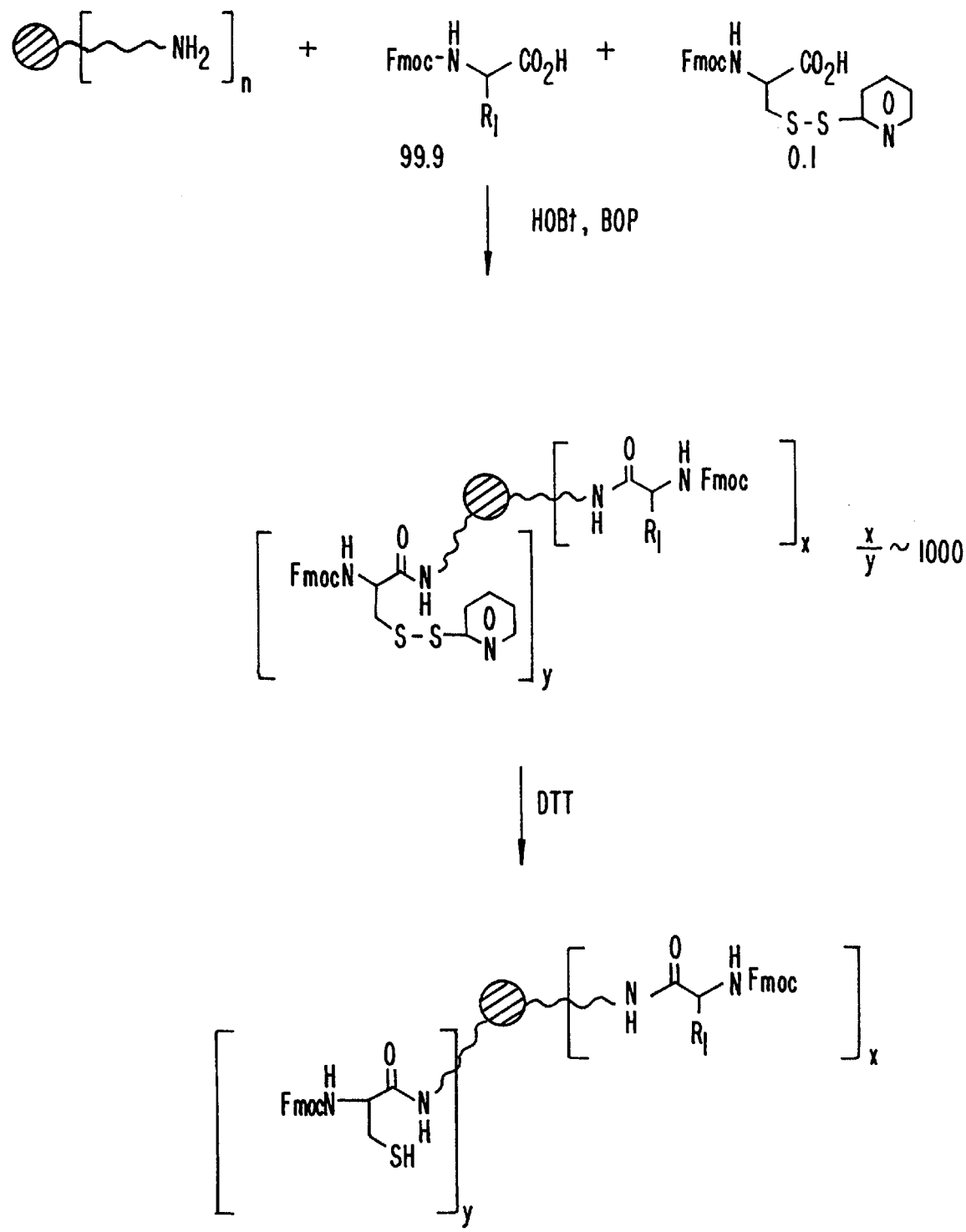
Figure 3D:
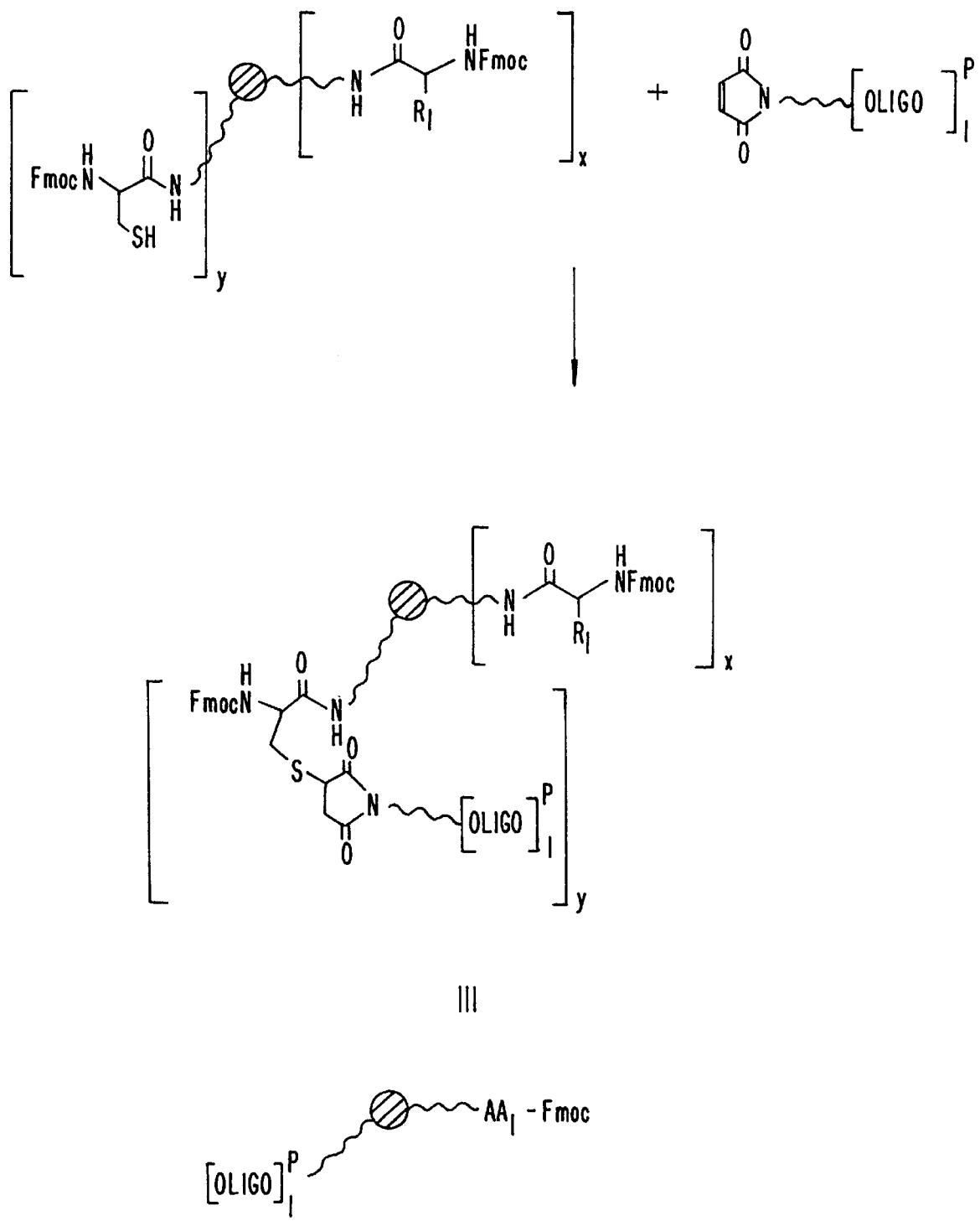
Figure 3E:
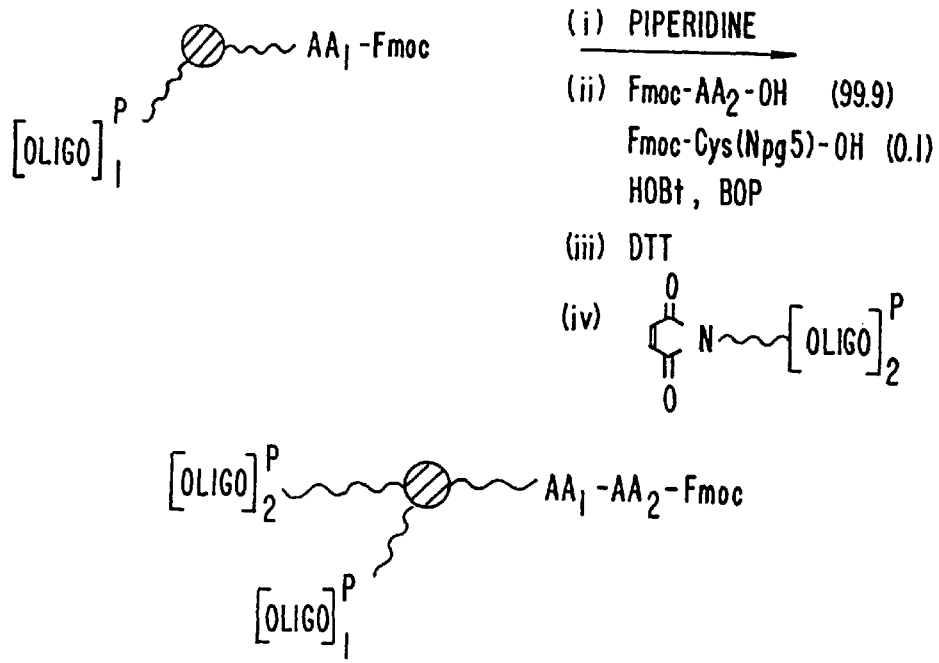
Figure 3F:
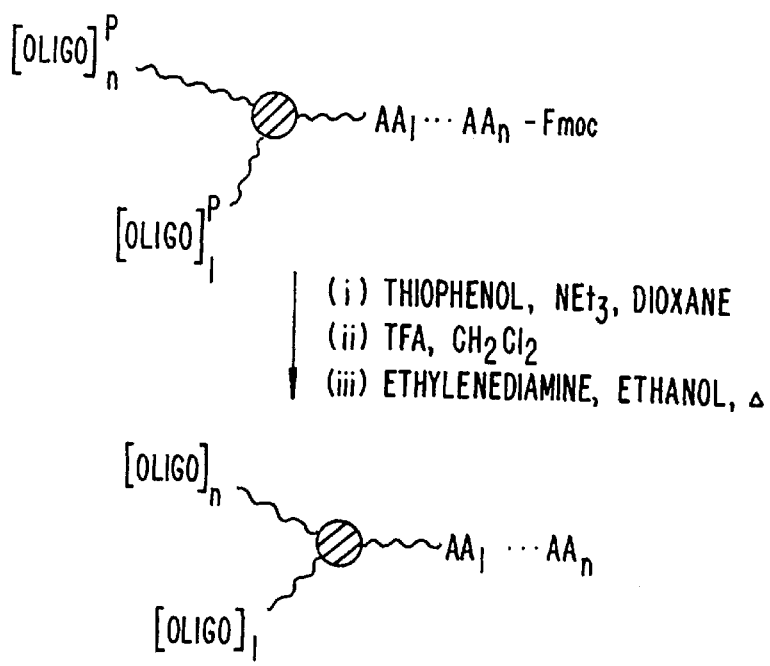

For example, one might attach microscopically recognizable, alphanumeric tags to each bead (see FIG. 2): "A1" means that the bead participated in the A-monomer reaction at step 1, "C2" means that the bead participated in the C-monomer reaction at step 2, and "B3" means B-monomer was added in step 3, and so on. At the end of the 3-step synthesis, the bead would have three tags attached, e.g., A1, C2, and B3, indicating that the sequence of the peptides on the bead is ACB. This scheme requires a number of distinct identifier tags equal to at most the product of the number of different monomers and the number of synthesis steps (nine in this example). The number of identifier tags is reduced if the symbols are attached to one another in the order of the steps: A, A-C, A-C-B. In this case only as many identifier tags are needed as monomers. One builds the identifier tag in much the same way as the peptides, so as to preserve a record of what was monomer was added, and in which addition step.

The identifier tags therefore identify each monomer reaction that an individual library member or solid support has experienced and record the step in the synthesis series in which each monomer is added. The tags may be attached immediately before, during, or after the monomer addition reaction, as convenient and compatible with the type of identifier tag, modes of attachment, and chemistry of oligomer synthesis. The identifier tag is added when the solid supports that have undergone a specific monomer addition step are physically together and so can be tagged as a group, i.e., prior to the next pooling step.

In some cases, of course, when only a small number of monomer units of an oligomer are varied, one may need to identify only those monomers which vary among the oligomers, as when one wants to vary only a few amino acids in a peptide. For instance, one might want to change only 3 to 6 amino acids in peptides 6 to 12 amino acids long, or one might want to change as few as 5 amino acids in polypeptides up to 50 amino acids long. One may uniquely identify the sequence of each peptide by providing for each solid support an identifier tag specifying only the amino acids varied in each sequence, as will be readily appreciated by those skilled in the art. In such cases, all solid supports may remain in the same reaction vessel for the addition of common monomer units and apportioned among different reaction vessels for the addition of distinguishing monomer units.

The identifier tag can be associated with the oligomer through a variety of mechanisms, either directly, through a linking molecule, or through a solid support upon which the oligomer is synthesized. In the latter mode, one could also attach the tag to another solid support that, in turn, is bound to the solid support upon which the oligomer is synthesized.

IV. Types of Identifier Tags

The identifier tag may be any recognizable feature that is, for example: microscopically distinguishable in shape, size, color, optical density, etc.; differently absorbing or emitting of light; chemically reactive; magnetically or electronically encoded; or in some other way distinctively marked with the required information, and decipherable at the level of one (or few) solid supports. In one embodiment, each bead or other solid support in the library incorporates a variety of fluorophores, or other light addressable type of molecules, the spectral properties of which can be changed and therefore used to store information. In one such mode, a bead incorporates a variety of fluorophors, each of which can be selectively photobleached, and so rendered incapable of fluorescence or of diminished fluoresence. During each coupling step, the bead is irradiated (or not) to photobleach (or not) one or more particular types of fluorophors, thus recording the monomer identity in the oligomer synthesized. See Science 255: 1213 (Mar. 6, 1992), incorporated herein by reference.

One can construct microscopically identifiable tags as small beads of recognizably different sizes, shapes, or colors, or labeled with bar codes. The tags can be "machine readable" luminescent or radioactive labels. The identifier tag can also be an encodable molecular structure. The information may be encoded in the size (the length of a polymer) or the composition of the molecule. The best example of this latter type of tag is a nucleic acid sequence, i.e., RNA or DNA assembled from natural or modified bases.

Synthetic oligodeoxyribonucleotides are especially preferred information-bearing identifier tags. Oligonucleotides are a natural, high density information storage medium. The identity of monomer type and the step of addition is easily encoded in a short oligonucleotide sequence and attached, for example, to each peptide synthesis bead. When a single bead is isolated by screening, e.g., for receptor binding, the attached oligonucleotides can be amplified by methods such as PCR (see *PCR Protocols: A Guide to Methods and Applications.* (Innis, M, Gelfand, D., Sninsky, J. and White, T., Academic Press, San Diego 1990), incorporated herein by reference), or by other nucleic acid amplification techniques, such as the ligase chain reaction and the self-sustained sequence replication system. The amplified product can be easily sequenced or otherwise identified to decode the identity of the peptide on the bead. For this purpose, one can use any of a variety of sequencing methods, including sequencing by sequence-specific probe hybridization.

Alternatively, the information may be encoded in the length rather than, or in addition to, the sequence of the oligonucleotide. If only oligonucleotide length is utilized to represent each specific monomer addition to the oligomer, then the identity of the oligomer can be decoded by amplifying the oligonucleotide, as described above, and identifying the labels through any of a variety of size-separation techniques, including polyacrylamide gel electrophoresis or capillary electrophoresis.

There are several ways that oligonucleotides can be used as identifier tags. The oligonucleotides can be assembled base-by-base before, during, or after the corresponding oligomer (e.g., peptide) synthesis step. In one case of base-by-base synthesis, the tag for each step is a single nucleotide, or at most a very few nucleotides (i.e., 2 to 5). This strategy preserves the order of the steps in the linear arrangement of the oligonucleotide chain grown in parallel with the oligomer. To preserve the chemical compatibility of the parallel synthetic steps (oligonucleotides and peptides, for example), one can modify the standard synthesis chemistries.

One variation of base-by-base assembly is the block-by-block approach; encoded sets of nucleotides ("codons") of 5 to 10 or more bases are added as protected, activated blocks. Each block carries the monomer-type information, and the order of addition represents the order of the monomer addition reaction. Alternatively, the block may encode the oligomer synthesis step number as well as the monomer-type information.

One could also attach protected (or unprotected) oligonucleotides containing amplification primer sites, monomer-specific information, and order-of-reaction information, from 10 to 50 to 150 bases in length, at each step. At the end of a series of n oligomer synthesis steps, there would be n differently encoded sets of oligonucleotide identifier tags associated with each oligomer sequence. After identifying the oligomers with ligand activity, the associated oligonucleotides are amplified by PCR and sequenced to decode the identity of the oligomer.

V. Linking the Identifier Tag(s) to the Oligomer

The identifier tags may be attached to chemically reactive groups (unmasked thiols or amines, for example) on the surface of a synthesis support functionalized to allow synthesis of an oligomer and attachment or synthesis of the oligonucleotide identifier tag. The tags could also be attached to monomers that are incorporated into a small proportion of the oligomer chains; or as caps on a small number of the oligomer chains; or to reactive sites on linkers joining the oligomer chains to the solid support.

In one embodiment, the solid supports will have chemically reactive groups that are protected using two different or "orthogonal" types of protecting groups. The solid supports will then be exposed to a first deprotection agent or activator, removing the first type of protecting group from, for example, the chemically reactive groups that serve as oligomer synthesis sites. After reaction with the first monomer, the solid supports will then be exposed to a second activator which removes the second type of protecting group, exposing, for example, the chemically reactive groups that serve as identifier tag attachment sites. One or both of the activators may be in a solution that is contacted with the supports.

In another embodiment, the linker joining the oligomer and the solid support may have chemically reactive groups protected by the second type of protecting group. After reaction with the first monomer, the solid support bearing the linker and the "growing" oligomer will be exposed to a second activator which removes the second type of protecting group exposing the site that attaches the identifier tag directly to the linker, rather than attachment directly to the solid support.

When activators or deprotection agents are incorporated into the method of preparing a synthetic peptide library having a plurality of different members, each member comprising a solid support attached to a different single peptide sequence and an oligonucleotide identifier tag identifying said peptide sequence, the method comprises: a) apportioning the solid supports among a plurality of reaction vessels; b) reacting the solid supports with a solution in each reaction vessel and treating sequentially with (1) a first activator to remove a first type of protective group from the solid support, (2) a first amino acid or peptide to couple said amino acid or peptide to said solid support at sites where said first type of protective group has been removed; (3) a second activator to remove a second type of protective group from the solid support; and (4) a first nucleotide or oligonucleotide tag to couple said tag at sites where said second type of protective group has been removed; c) pooling the solid supports; d) apportioning the pooled solid supports among a plurality of reaction vessels; and e) repeating step (b) to couple a second amino acid or peptide and a second nucleotide or oligonucleotide tag to said solid support.

As noted above, the invention can also be carried out in a mode in which there is no solid support, and the tag is attached directly (or through a linker) to the oligomer being synthesized. The size and composition of the library will be determined by the number of coupling steps and the monomers used during the synthesis. Those of skill in the art recognize that either the tag or the monomer may be coupled first, in either embodiment.

Another possible embodiment is the use of two solid supports, such as beads, that are physically linked together, one with synthesis sites (or linkers) for the oligomer and one with attachment sites (or linkers) for the identifier tags. This arrangement allows the segregation of oligomers and identifier tags into discrete "zones" and permits the use of widely different chemically reactive groups and chemistries for attachment. The solid supports can be derivatized separately and then linked under conditions where all or nearly all of the synthesis solid supports will have a tag-attachment solid support in tow. The solid supports can be of different sizes, as for example a large synthesis bead with several (or many) smaller tag-attachment beads linked. In one embodiment, the first solid support will have at least one attached amino acid and the second solid support will have at least one attached nucleotide.

The mode of linking the two beads is constrained by the chemistry of oligomer synthesis. The most obvious means of linking the beads is with a heterobifunctional cross-linking agent (for examples of such agents, see *Pierce ImmunoTechnology Catalog and Handbook* pp. E10–E18 (1991)) interacting with the dominant chemically reactive groups on each species of solid support.

VI. Encoding the Identifier Tag Information

The choice of bases used in an oligonucleotide identifier tag is dictated by the chemistry of oligomer synthesis. For example, the use of strong acid to deprotect peptides would depurinate nucleic acids. Therefore, when standard chemistries for peptide synthesis are employed, the pyrimidines C and T could be used in a binary code. Thus, in a preferred embodiment, the identifier tag will be an oligopyrimidine sequence.

In another embodiment, the lability of purine nucleotides to strong acid may be overcome through the use of the purine nucleoside analogs, such as 7-deaza-2'-deoxyadenosine and 7-deaza-2'-deoxyguanosine (see Barr et al., *BioTechniques* 4:428–432 (1986), and Scheit, *Nucleotide Analogs: Synthesis and Biological Function* pp. 64–65 (John Wiley and Sons, New York), both of which are herein incorporated by reference). Use of these or other analogs would permit the use of a quaternary or other, as opposed to a binary, encoding scheme.

Information retrieval from oligonucleotide identifier tags is possible through various encryption schemes, two of which are described below. In the first, the oligomer sequence information is at least in part encoded in the length of the oligonucleotide. Each different monomer added at a given step in the oligomer synthesis may be represented by an oligonucleotide tag of unique length. The oligonucleotide inherently contains amplification sites, such as PCR priming sequences, characteristic of the given step-number in the oligomer synthesis. Determination of the oligomer composition at any given position in the sequence then involves amplifying the tag using the PCR priming sequence characteristic for that step in the synthesis and size-separating the amplification products utilizing techniques well known in the art, such as gel or capillary electrophoresis (using the tagging oligonucleotides as standards). This embodiment is particularly useful when one desires to make a library of compounds related to a lead sequence. One need only tag during steps in which a site being analoged is synthesized.

Figure 4:
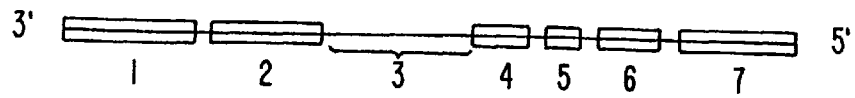
FIG. 4 is a schematic representation of one example of an oligonucleotide tag.

In addition to length, oligomer sequence information can also be encoded in the sequence of bases comprising the oligonucleotide tag. This type of encryption is of value not only in the embodiment in which one attaches a different oligonucleotide tag at each coupling step but also in the embodiment in which one extends an oligonucleotide tag at each coupling step. For example, as shown in FIG. 4, one may use oligonucleotides of up to about 100 bases (or somewhat longer), each having seven regions, as described below.

Region 1 is a 3'-PCR primer site (20 to 25 bases). This site is used in conjunction with another PCR site (at the 5'-end of the oligonucleotide) to prime amplification by PCR. Other amplification methods may also be used.

Region 2 is a "step-specific" DNA sequencing primer site (15–20 bases). This site is specific for the particular numbered step in the synthesis series. All the oligonucleotides added to all the beads at a particular step will have this sequence in common. Each numbered step will have a highly specific primer site representing that step.

Region 3 is a spacer (20–30 bases). A spacer segment of variable length, but preferably 20 to 30 bases long, places the coding site sufficiently distant from the sequencing primer site to give a good "read" through the monomer encoding or identification region.

Region 4 is a monomer identification region (8 bases). Each base in this string represents one bit of binary code, where, for example, T=0 and C=1. Each set of step-specific identifier tags consists of 8 bases with a 1 (C) or a 0 (T) at each of the 8 positions. These may be thought of as switches set to "on" or "off" at the different positions. Each monomer type is encoded by a mixture of 1 to 8 of these "switches."

Region 5 is a step number confirmation region (4 bases plus 2 bases on either side for region distinction). Four bits in this short stretch encode the step number. This is redundant to the sequencing primer but can be used to confirm that the proper primers were used and that the right step is decoded.

Region 6 is a repeat of the monomer identification region (8 bases). This region has the same information as region 4, and is used to confirm monomer identity. Installing this second monomer encoding region also increases the probability that a good sequencing "read" will be obtained.

Region 7 is a 5'-PCR primer site (20 to 25 bases). This site serves as a site for annealing the second PCR primer for amplification of the sequence. The length of oligonucleotides with all seven of these features, some of which are optional, will commonly be between 75 and 125 bases.

An 8 bit format can encode 256 different monomer types. The number of steps that can be encoded is determined by the number of step-specific sets (8 per set) of oligonucleotides on hand. With 10 sets (80 oligos) one can encode up to 256 different monomers assembled into oligomers up to 10 units long (thus providing encoding capability for up to $256^{10}=1.2\times10^{24}$ oligomer sequences). The coded identifier tags may be used so that each monomer is assigned a specific binary number (e.g., Ala=00000001, Gly=00000110, etc.).

The appropriate oligonucleotides are combined to give the correct binary code.

VII. Recovering and Decoding the Identifier Tag Information

When specific beads are isolated in a receptor screening experiment, the beads can be segregated individually by a number of means, including: infinite dilution, micromanipulation, or preferably, fluorescence activated cell sorting (FACS), although, with respect to the present invention, FACS is more accurately "fluorescence activated oligomer or solid support sorting" (see *Methods in Cell Biology,* Vol. 33 (Darzynkiewicz, Z. and Crissman, H. A., eds., Academic Press); and Dangl and Herzenberg, *J. Immunol. Methods* 52:1–14 (1982), both incorporated herein by reference). Once the desired beads have been isolated, one needs to identify the tag to ascertain the sequence of the oligomer on the bead.

To facilitate tag identification, one has a variety of options. For instance, one could read the tag directly from the bead by sequencing or hybridization, if the tag is an oligonucleotide. One can also amplify oligonucleotide tags to facilitate tag identification. The oligonucleotide identifier tags carried by a single solid support or oligomer can be amplified in vivo, by cloning, or in vitro, e.g., by PCR. If the limit of detection is on the order of 100 molecules, then at least 100 or more copies of each oligonucleotide tag on a bead would be required. Copies of the tag are produced, either as single stranded oligonucleotides, double-stranded nucleic acids, or mixtures of single and double-stranded nucleic acids, by any of a variety of methods, several of which are described below, and the amplified material is sequenced. In the embodiment of the invention in which a separate and distinct oligonucleotide tag is added at each monomer addition step (as opposed to extending an existing tag at each step), one can amplify all tags at once and then divide the amplified material into as many separate sequencing reactions as there were oligomer synthesis steps (employing a different sequencing primer for each type of tag). In this embodiment, one could also design the tags so that each tag could be amplified separately from the other tags by appropriate choice of primer sequences. The sequencing reactions are performed and run on a standard sequencing gel, and the oligomer sequence is deduced from the code revealed in the resulting sequence information.

An alternative strategy is to use common PCR primers and common sequencing primers (the sequencing primer may even overlap completely or partially with a PCR primer site) and identify the step by hybridization to oligonucleotide probes that are complementary to each step-specific sequence in the oligonucleotides from the bead. A single set of sequencing reactions is performed on all of the amplified oligonucleotides from a single bead, and the reaction products are run in a single set of lanes on a gel. The reaction products are then transferred to a suitable hybridization membrane and hybridized to a single step-specific probe (see Maniatis et al., Cold Spring Harbor Laboratory, Cold Spring Harbor, N.Y. (1982), which is incorporated herein by reference). After detection of the resulting signal, the probe is washed from the membrane and another step-specific probe is hybridized. One could also use the procedure described in EPO publication No. 237,362 and PCT publication No. 89/11548, each of which is incorporated herein by reference.

Parallel hybridization provides an alternative to sequential hybridization. The sequencing reactions are divided into a number of aliquots equal to the number of peptide synthesis steps and run in a separate set of lanes for each on the sequencing gel. After transfer of the reaction products to a suitable membrane, the membrane is cut to separate the sets of lanes. Each lane set is then hybridized to one of a plurality of step-specific oligonucleotide probes (see "Uniplex DNA sequencing" and "Multiplex DNA sequencing," in *Plex Luminescent Kits Product Catalog,* Bedford, Mass., 1990, incorporated herein by reference).

As noted above, a single synthesis solid support (or an attached bead bearing a tag, or in solution in a "well") may only comprise a few hundred copies of each oligonucleotide tag. These tags may be amplified, e.g., by PCR or other means well known to those skilled in the art, to provide sufficient DNA to be sequenced accurately. The ability to decode the oligomers depends on the number of available oligonucleotide identifier tags, the level of amplification that can be achieved from the available tags, and the accuracy of sequencing that amplified DNA.

The most commonly used in vitro DNA amplification method is PCR. Alternate amplification methods include, for example, nucleic add sequence-based amplification (Compton, *Nature* 350:91–92 (1991), incorporated herein by reference) and amplified antisense RNA (Van Gelder et al., *Proc. Nat. Acad. Sci. USA* 85:7652–7656 (1988), incorporated herein by reference), and the self-sustained sequence replication system (3SR, see Guatelli et al., *Proc. Natl. Acad. Sci. USA* 87: 1874–1878 (1990), incorporated herein by reference).

If PCR amplification of an oligonucleotide identifier tag is employed, one may encounter "PCR product contamination," caused by the product of one PCR reaction contaminating a subsequent PCR reaction mixture designed to amplify other tags having the same PCR primer binding sites. One may prevent this problem by introducing lability into the product sequences and treating subsequent reactions so as to destroy potential contamination carried over from previous reactions. A specific example of this strategy, for which commercial kits are sold by PECI and Life Technologies, is to introduce dUMP into the product. Treating each new PCR reaction with uracil-N-glycosidase degrades any dU-containing DNA present, preventing amplification of the contaminant. The-template DNA, which contains no dU (only dT) is not affected. Of course, the glycosidase is removed or inactivated before amplification is begun.

Some of the tags described above for peptide synthesis have the unusual characteristic of containing only pyrimidines. This means that the uracil glycosidase strategy (Perkin Elmer Cetus Instruments (PECI) Catalog, Alameda (1991), incorporated herein by reference) will work on only half of the strands produced—those containing T's (or U's). One cannot introduce dUMP into the complementary, purine-only strand; however, the purine strand is highly vulnerable to acid depurination and alkaline-mediated scission of the backbone. The combination of these treatments can greatly reduce problems with product contamination. Another approach to preventing carryover contamination involves incorporation of a restriction site (EarI could be used for polypyrimidine tags) into the oligonucleotide tag and digestion with the corresponding restriction enzyme prior to amplification of a reaction suspected of being contaminated with the tag. This method only works if the tag to be amplified will not be cleaved by the enzyme, as would generally be the case for a single stranded oligonucleotide tag.

For sequencing amplified DNA, one usually desires to generate single stranded templates. This generation may be accomplished by any of several means. One such means is asymmetric PCR, where an excess of one of the primers is used to amplify one strand to a level 10 to 100-fold higher than the other (see, for example, U.S. Pat. No. 5,066,584, incorporated herein by reference). Another means of providing a single stranded template is to by biotinylate one of the primers and purify or remove the resulting strand by adsorption to immobilized streptavidin (*Pierce Immunotechnology Catalog and Handbook*, 1991, incorporated herein by reference). Yet another means involves generation of RNA transcripts (representing only one of the strands) from an RNA polymerase promoter and sequencing the transcripts with reverse transcriptase (Sommer et al., Chapter 25, In *PCR Protocols: A Guide to Methods and Applications*, supra, incorporated herein by reference). If the tags are composed of only pyrimidine nucleotides, then all purine strands can be eliminated by acid/base treatment, leaving the pyrimidine strand for sequencing.

The use of separate sequencing primers for each step-specific oligonucleotide requires a separate, conventional sequencing reaction for each step-specific primer. Using primers that are differentially labeled would allow the identifier tags from a single solid support to be sequenced in a single reaction and run in a single lane set (2 lanes) on a gel. There are now commercially available primers labeled with distinguishable fluorophores that are suitable for this purpose (ABI Catalog, incorporated herein by reference). Sets of chemiluminescent labels now distributed commercially may also be used (Bronstein et al., *BioTechniques* 8: 310–314 (1990), incorporated herein by reference).

DNA sequencing enzymes which may be employed in the present invention include Taq DNA polymerase, *E. coli* DNA polymerase I (or the Klenow fragment), T7 polymerase, Sequenase™ and Sequenase II™ (Modified T7 DNA polymerases), Bst DNA polymerase, and reverse transcriptase (from AMV, MMLV, RSV, etc., see *USB Enzymes for DNA Sequencing*, U.S. Biochemical Corp, 1991, Cleveland Ohio, incorporated herein by reference).

The sequence of an oligonucleotide tag may also be identified by a high fidelity DNA hybridization technique. To this end, very large scale immobilized polymer synthesis with oligonucleotides may be useful (see PCT patent publication Nos. 92/10587 and 92/10588, each of which is incorporated herein by reference).

VIII. Screening Receptors with Synthetic Oligomer Libraries

The tagged synthetic oligomer libraries of the present invention will have a wide variety uses. By way of example, these libraries can be used in determining peptide and nucleic acid sequences that bind to proteins, finding sequence-specific binding drugs, identifying epitopes recognized by antibodies, and evaluating a variety of drugs for clinical and diagnostic applications, as well as combinations of the above. Peptides as short as about five amino acids long might be useful in receptor-binding studies, for example.

Synthetic oligomers displayed on small beads can be screened for the ability to bind to a receptor. The receptor may be contacted with the library of synthetic oligomers, forming a bound member between an receptor and the oligomer able to bind the receptor. The bound member may then be identified. As one example, the receptor may be an immunoglobulin.

The techniques for selection of individual beads displaying ligands on their surface are analogous to FACS methods for cloning mammalian cells expressing cell surface antigens or receptors. Therefore, methods for selecting and sorting beads will be readily apparent to those skilled in the art of cell sorting. For example, a receptor can be labelled with a fluorescent tag and then incubated with the mixture of beads displaying oligomers. After washing away unbound or non-specifically bound receptors, one can then use FACS to sort the beads and to identify and isolate physically individual beads showing high fluorescence.

Alternatively, affinity adsorption techniques can be employed in conjuction with the libraries of the invention. The mixture of beads can be exposed to a surface on which a receptor has been immobilized (see PCT patent publication No. 91/07087, incorporated herein by reference). After washing to remove unbound beads, one can then elute beads bound to the surface using conditions that reduce the avidity of the oligomer/receptor interaction (low pH, for example). The process of affinity adsorption can be repeated with the eluted beads, if desirable. Finally, individual beads are physically separated, for example, by limited dilution, by FACS, or by methods similar to those in which cells are incubated with a receptor coupled to small superparamagnetic beads and then cells expressing a ligand for the receptor are extracted using a high power magnet (see Miltenyi et al., *Cytometery* 11:231–238 (1990), incorporated herein by reference). Magnetically selected cells can be further analyzed and sorted using FACS. Radionucleotides may also serve to label a receptor.

Alternatively, the present invention can be used to generate libraries of soluble tagged oligomers, which can be used with a variety of screening methods. For instance, the oligomer library can be synthesized on beads with an identifying tag encoding the oligomer sequence. The microscopic beads are placed in individual compartments or wells that have been "nanofabricated" in a silicon or other suitable surface. The oligomers are cleaved from the beads and remain contained within the compartment along with the bead and the attached identifier tag(s). In one embodiment, the bottom surface is coated with the receptor, and after the addition of binding buffer and a known ligand for that receptor that is fluorescently labelled, one effectively has a solution phase competition assay for novel ligands for the receptor. The binding of the fluorescently labelled ligand to the receptor is estimated by confocal imaging of the monolayer of immobilized receptor. Wells with decreased fluorescence on the receptor surface indicate that the released oligomer competes with the labelled ligand. The beads or the tag in wells showing competition are recovered, and the oligonucleotide tag is amplified and sequenced to reveal the sequence of the oligomer.

The beads are loaded in the wells by dispersing them in a volume of loading buffer sufficient to produce an average of one bead per well. In one embodiment, the solution of beads is placed in a reservoir above the wells, and the beads are allowed to settle into the wells. Cleavage of the oligomers from the beads may be accomplished using chemical or thermal systems, but a photocleavable system is preferred.

Recovery of identifier-tagged beads from positive wells may be effectuated by a micromanipulator plucking out individual beads. However, a preferred mode involves the use of beads that have been previously labelled with a fluorescent tag. A laser of the appropriate wavelength is then used to bleach the resident beads in only the positive wells. All the beads are then removed en masse and sorted by FACS to identify the bleached positives. The associated tags may then be amplified and decoded.

In a variation of this assay, the oligomer and tag may be synthesized attached to a common linker, which, in turn, is bound to the solid support. After placing the beads in the wells, one can cleave the linker from the bead, producing a tagged oligomer in solution. An immobilized receptor, such as a receptor bound to a bead or a receptor immobilized on one surface of the well, can be screened in a competition assay with the oligomer and a fluorescently labeled ligand. Instead of recovering the beads, one may recover the beads bearing immobilized receptors and sort the beads using FACS to identify positives (diminished fluorescence caused by the library oligomer competing with the labeled ligand) or one can determine the fluorescence emitting from the well surface coated with receptor. The associated identifier tag may then be amplified and decoded.

In a third variation of this approach, soluble tagged oligomers, produced either by cleavage of the linked oligomer and tag from the solid support as described above, or synthesized by the VLSIPS™ method described above, or synthesized in solution without a solid support, are incubated with an immobilized receptor. After a wash step, the bound, tagged oligomers are released from the receptor by, e.g., acid treatment. The tags of the bound oligomers are amplified and decoded.

IX. An Automated Instrument for Oligomer Synthesis and Tagging

The coupling steps for some of the monomer sets (amino acids, for example) require a lengthy incubation time, and a system for performing many monomer additions in parallel is desirable. This can be accomplished with an automated instrument able to perform 50 to 100 parallel reactions (channels). Such an instrument is capable of distributing the reaction mixture or slurry of synthesis solid supports, under programmable control, to the various channels for pooling, mixing, and redistribution.

Much of the plumbing typical of peptide synthesizers is required, with a large number of reservoirs for the diversity of monomers and the number of tags (up to 80 for a 10 step synthesis, in one embodiment) employed. The tag dispensing capability will translate simple instructions into the proper mixture of tags and dispense that mixture. Monomer building blocks will also be dispensed, as desired, as specified mixtures. Reaction agitation, temperature and time control may be provided. An appropriately designed instrument may also serve as a multi-channel peptide synthesizer capable of producing 1 to 50 mgs (crude) of up to 100 specific peptides for assay purposes. See PCT patent publication 91/17823, incorporated herein by reference.

EXAMPLE I

Synthesis on Glass Beads of 4 Fluorescently Tagged Pentapeptides

A. Derivatization of Glass Beads

About 0.5 g of 3–10 um diameter silica beads (Polyscience) were washed with refluxing 10% aqueous $HNO_3$ for 20 min. The beads were pelleted and washed with distilled water (5×) and methanol (3×) and dried at 125 degrees C. for 12 hours. Beads were vortexed with a 5% solution of aminopropyltriethoxysilane in acetone for 10 hours, pelleted and then washed with acetone (2×), ethanol (5×), and methylene chloride (2×) and dried at 125 degrees C. for 45 min. Beads were suspended in dry DMF (1 mL) containing diisopropylethylamine (17 μl, 100 μmoles) and a solution of Fmoc-b-alanine, pentafluorophenyl ester (200 mg, 420 μmoles, Peninsula Labs) in distilled water (1.5 mL) was added. After vortex treatment for 11 hours, the beads were pelleted and washed with DMF (3×) and methylene chloride (2×). Beads were treated with a 10% solution of acetic anhydride in DMF containing 0.05 mol of 4-dimethylaminopyridine to cap any underivatized aminopropyl groups, and then washed with DMF (2×) and methylene chloride (2×). Beads were vortexed with a 20% solution of piperidine in DMF and the release of the Fmoc-piperidine adduct quantitated by monitoring the absorbance spectrum of the supernatant at 302 nm ($^e 302=7800$ $M^{-1}$ $cm^{-1}$). An estimate of the degree of substitution of 10 μmoles of amino groups/g beads was thus obtained. Finally, the beads were washed with ethanol (5×) and methylene chloride (2×) and then dried at 85 degrees C. for 12 hours.

B. Preparation of Boc-Gly-L-Phe-L-Leu-OH

Glycyl-L-Phenylalanyl-L-leucine (552 mg, 1.5 mmol, Bachem) was dissolved in a solution containing distilled water (10 mL) and 1 M NaOH (1.5 mL). The solution was cooled in an ice bath and was treated with a solution of di-tert-butyl pyrocarbonate (337 mg, 1.5 mmol) in p-dioxane (12 mL). A white precipitate rapidly formed but redissolved after stirring at room temperature for 4 hours. The solution was concentrated to dryness in vacuo the residue taken up in water (5 mL), and the pH adjusted to 2.5 by the addition of 1 M $KHSO_4$. The aqueous suspension was extracted with EtOAc (2×, 15 mL), the organic layer separated, and dried over $MgSO_4$. After removal of the solvent in vacuo the residue was triturated with hexane to afford Boc-Gly-L-Phe-L-Leu-OH as a white solid (yield=642 mg, 98%).

C. Preparation of Gly-L-Phe-L-Leu Beads

Boc-Gly-L-Phe-L-Leu-OH (44 mg, 0.1 mmol), benzotriazol-1-yloxytris(dimethylamino)phosphonium hexafluorophosphate (44 mg, 0.1 mmol) and 1-hydroxybenzotriazole hydrate (14 mg, 0.104 mmol) were dissolved in dry DMF (1 mL). Diisopropylethylamine (20 μl, 0.115 mmol) was then added and 0.65 mL of this solution was immediately transferred to a microcentrifuge tube containing 80 mg of amino derivatized glass beads. The sealed tube was vortexed for 3.5 hours, and the beads were then pelleted and washed with DMF (3×) and methylene chloride (2×). The beads were then deprotected with a 50% solution of trifluoroacetic acid in methylene chloride for 30 min., washed with methylene chloride (2×), ethanol (2×), and methylene chloride (2×), and dried at 55 degrees C. for 1 hour.

D. Preparation of Gly-Gly-L-Phe-L-Leu Beads (SEQ ID NO:10)

Fmoc-glycine pentafluorophenyl ester (46 mg, 0.1 mmol) was dissolved in dry DMF (1 mL) containing diisopropylethylamine (17 μl, 0.1 mmol). About 0.65 mL of this solution was added to 20 mg of Gly-L-Phe-L-Leu beads in a microcentrifuge tube, and the tube was vortexed for 3 hours. The beads were pelleted and washed with DMF (4×) and methylene chloride (2×). Deprotection was effected by treatment with a 20% solution of piperidine in DMF for 30 min. The beads were washed with DMF (2×), ethanol (2×), and methylene chloride (2×) and dried at 60 degrees C. for 4 hours.

E. Preparation of L-Pro-Gly-L-Phe-L-Leu Bead (SEQ ID NO:11)

Fmoc-L-proline pentafluorophenyl ester (50 mg, 0.1 mmol) was dissolved in dry DMF (1 mL) containing diisopropylethylamine (17 μl, 0.1 mmol). About 0.65 mL of this solution was added to 20 mg of Gly-L-Phe-L-Leu beads in a microcentrifuge tube, and the tube was vortexed for 3 hours. The beads were pelleted and washed with DMF (4×) and methylene chloride (2×). Deprotection was effected by treatment with a 20% solution of piperidine in DMF for 30 min. The beads were washed with DMF (2×), ethanol (2×), and methylene chloride (2×) and dried at 60 degrees C. for 4 hours.

F. Fluorescein Staining of Gly-Gly-L-Phe-L-Leu Beads

About 5.4 mg of Gly-Gly-L-Phe-L-Leu beads were suspended in 450 μl of aqueous borate buffer (pH 8.5) and 54

μl of a 10 μM solution of fluorescein isothiocyanate (FITC) added. After vortex treatment for 1.5 hours, the beads were washed with buffer (5×), ethanol (2×), and methylene chloride (2×). FACS analysis indicated that approximately 10% of available amino groups had been titrated with FITC.

G. Co-coupling of L-Tyrosine and Biotin to Mixture of L-Pro-Gly-L-Phe-L-Leu and FITC Labelled Gly-Gly-L-Phe-L-Leu Beads 5 mg of FITC labelled Gly-Gly-L-Phe-L-Leu beads and 5 mg L-Pro-Gly-L-Phe-L-Leu beads were mixed together in a single tube, vortexed with a 0.1 mM solution of diisopropylethylamine in methylene chloride, and the suspension was divided into two equal portions. The beads were pelleted, and to one portion was added a solution containing Fmoc-O-tert-butyl-L-tyrosine pentafluorophenyl ester (59 mg, 95 μmol), N-hydroxysuccinimidobiotin (1.7 mg, 5 μmol) and diisopropylethylamine (17 μl, 100 μmol) in dry DMF (1 mL). After vortexing for 3 hours the beads were washed with distilled water (2×), ethanol (2×), methylene chloride (2×) and DMF (1×). Fmoc deprotection was effected by treatment with a 20% solution of piperidine in DMF for 30 min., and tert-butyl side chain protecting groups were removed by treatment with 25% trifluoroacetic acid in methylene chloride for 30 min. The pelleted beads were washed with methylene chloride (2×), ethanol (2×), and TBS (1×).

H. R-Phycoerythrin Staining of Biotinylated L-Tyr-(Gly/L-Pro)-Gly-L-Phe-L-Leu Beads (Mixture of SEQ ID NO:12 and SEQ ID NO:13)

Biotinylated L-tyrosine beads from (G) above were suspended in TBS (0.5 mL) and treated with 10 μl of R-phycoerythrin-avidin conjugate (Molecular Probes) for 30 min. Pelleted beads were washed with TBS (5×).

I. Co-coupling of L-Proline and Biotin to Mixture of L-Pro-Gly-L-Phe-L-Leu and FITC Labelled Gly-Gly-L-Phe-L-Leu Beads (Mixture of SEQ ID NO:15 and SEQ ID NO:14)

5 mg of a mixture of L-Pro-Gly-L-Phe-L-Leu and FITC labelled Gly-Gly-L-Phe-L-Leu beads were treated with a solution containing Fmoc-L-proline pentafluorophenyl ester (48 mg, 95 μmol), N-hydroxysuccinimidobiotin (1.7 mg, 5 μmol), and diisopropylethylamine (17 μl, 100 μmol) in dry DMF (1 mL). After vortex treatment for 3 hours, the beads were washed with DMF (2×), ethanol (2×), methylene chloride (2×), and DMF (1×). Fmoc deprotection was effected by treatment with a 20% solution of piperidine in DMF for 30 min., and by way of control, the beads were treated with 25% trifluoroacetic acid in methylene chloride for 30 min. The pelleted beads were washed with methylene chloride (2×), ethanol (2×), and TBS (1×).

J. Tri-Color Staining of Biotinylated L-Pro-(Gly/L-Pro)-Gly-L-Phe-L-Leu Beads

Biotinylated L-proline beads from (i) above are suspended in TBS (0.5 mL) and treated with 20 μl Tri-Color: streptavidin conjugate (Caltag Labs) for 30 min. Pelleted-beads are washed with TBS (5×).

K. Selection of Beads Containing Peptide Ligands for Monoclonal Antibody 3E7

Monoclonal antibody 3E7 was raised against the opioid peptide beta-endorphin. The binding specificity of MAb 3E7 has been well characterized by solution assays with chemically synthesized peptides. The equilibrium binding constants (Kd) of the peptides considered here are as follows: YGGFL is 6.6 nM; and YPGFL, PPGFL, and PGGFL are each >1 mM; thus, only the peptide YGGFL shows appreciable affinity for the antibody.

A mixture of beads containing either YGGFL, YPGFL, PGGFL, or PPGFL and their respective tags (see above) are added in phosphate buffered saline (PBS) containing monoclonal antibody 3E7 that has been previously conjugated to colloidal superparamagnetic microbeads (Miltenyi Biotec, West Germany). After a 16 hr incubation at 4 degrees C., beads which bind the 3E7 antibody are selected using a high strength magnet. The selected beads are then analyzed by flow cytometry. Analysis of the selected beads reveals that they contain both fluorescein and R-phycoerythrin, indicating that only beads displaying the peptide YGGFL are selected by the 3E7 antibody.

EXAMPLE 2

Synthesis on Glass Beads of 4 Pentapeptides Tagged with Oligonucleotide Identifiers A. Synthesis of Identifier Oligonucleotides (I)–(IV)

The oligonucleotide identifier tags (I)–(IV) have the sequences shown below. The regions complementary to the 5' and 3' PCR primers are underlined. The regions complementary to the step-specific sequencing primers are shown in lower case: there are two steps in this example. The monomer encoding region is shown in bold type: $CT_7$ encodes Gly, $TCT_6$ encodes L-Pro, and $TTCT_5$ encodes L-Tyr in this case. Thus oligos (I)–(IV) code respectively for Gly in position 2, L-Pro in position 2, L-Tyr in position 1, and L-Pro in position 1.

(I)  5'-$B^1B^2$-CTTTCT TCCTCTCCCTCTTTTCTCCTCTCTTTTTTCTC CTTCTTTTTTTCTCTCCCTCTCTC-CTCTCTCCCCTTTCTCTCCTTTCCCCTCTCCTCTC TCTCTTCTTTCC-3". (SEQ ID NO:1)

(II)  5'-$B^1B^2$-CTTTCT TCCTCTCCCTCTTTTCTCCTCTTCTTTTTTCTC CTTTCTTTTTTCTCTCCCTCTCTC-CTCTCTCccctttctctcctttc     ct CCTCTCCTCTCTCTCTTCTTTCC-3' (SEQ ID NO:2)

(III)  5'-$B^1B^2$-CTTTCT TCCTCTCCCTCTTTTCTCCTCTTTCTTTTTCTC CTTTTCTTTTTCTCTCCCTCTCTC-CTCTCTCtcttcctttcccctct      ctctct CCTCTCCTCTCTCTCTTCTTTCC-3' (SEQ ID NO:3)

(IV)  5'-$B^1B^2$-CTTTCT TCCTCTCCCTCTTTTCTCCTCTTCTTTTTTCTC CTTTCTTTTTTCTCTCCCTCTCTC-CTCTCTCtcttcctttcccctct      ctctct CCTCTCCTCTCTCTCTTCTTTCC-3' (SEQ ID NO:4)

where: $B^1$=p-Maleimido-$C_6H_4$—$(CH_2)_3$—C(O)NH—$(CH_2)_6$—O—$PO_2$—O—, and $B^2$=$CH_2$—CH[$(CH_2)_4$—NH-Biotin]-$CH_2$—O—$PO_2$—O—.

Oligos (I)–(IV) are synthesized on an ABI PCR-mate synthesizer using commercially available (Sigma) DMT-O-Me phosphoramidites. The $N^4$-amino group of cytidine is protected as the benzoyl derivative. The 5' terminal (B1) and penultimate (B2) phosphoramidites are respectively N-MMT-$C_6$-AminoModifer (Clonetech) and Biotin Phosphoramidite (Glen Research) for each oligonucleotide. The fully protected O-methyl phosphotriester oligomers are cleaved from the CPG support by treatment with concentrated $NH_4OH$ at 25 degrees C. for 1 hour. The crude products are purified by affinity chromatography on a monomeric avidin-agarose column (Pierce), and the full-length material is eluted with 2 mM biotin. The 5'-MMT group is removed by treatment with 80% acetic acid for 1 hour at 25 degrees C., and the solution is evaporated to dryness. The products are dissolved in PBS, pH 8.0, and treated with a 50-fold excess of succinimidyl 4-(p-maleimidophenyl) butyrate (Pierce) in DMF for 30 min. The modified, protected oligonucleotides are desalted by RP-HPLC, lyophilized and stored under nitrogen.

The primers used for PCR and sequencing are prepared in the normal fashion and are shown below:

5' PCR Primer 5'-TCCTCTCCCTCTTTTCTCCTCT-3' (corresponds to bases 7–28 of SEQ ID NO:1)

3' PCR Primer 5'-Biotin-GGAAAGAAGAGAGAGAGGAGAGG-3' (SEQ ID NO:5)

Step #1 Sequencing Primer 5'-AGAGAGGGGAAAGGAAGA-3' (SEQ ID NO:6)

Step #2 Sequencing Primer 5'-AGGAAAGGAGAGAAAGGG-3' (SEQ ID NO:7)

B. Preparation of Gly-Gly-L-Phe-L-Leu Beads Bearing Identifier Oligo (I)

5 mg of Gly-L-Phe-L-Leu beads are treated with a solution containing Fmoc-Gly-OH (99.95 μmol), Fmoc-Cys (Npys)-OH (0.05 μmol, Calbiochem), benzotriazol-1-yloxytris-(dimethylamino)phosphonium hexafluorophosphate (100 μmol), 1-hydroxybenzotriazole hydrate (100 μmol), and diisopropylethylamine (150 μmol) in dry DMF (1 mL) for 2 hours. The beads are washed with DMF (2×) and then with methanol (2×) and then treated with a 10 mM DTT solution in methanol for 30 min. to deprotect the cysteine residues. The beads are quickly washed with ice-cold methanol (2×), pelleted, and then reacted for 20 min with 100 μl of a 0.1 mM solution of oligo (I) in methanol. After washing with methanol (2×) and then with DMF (2×), the beads are deprotected for 20 min. with 20% piperidine in DMF. Finally, the beads are washed with DMF (2×), methanol (2×), and then methylene chloride (2×) and dried at 45 degrees C. for 1 hour.

C. Preparation of L-Pro-Gly-L-Phe-L-Leu Beads Bearing Identifier Oligo (II)

5 mg of Gly-L-Phe-L-Leu beads are treated as in (b) above, substituting Fmoc-L-Pro-OH and Oligo (II) for Fmoc-Gly-OH and Oligo (I), respectively.

D. Preparation of(O$^t$Bu)-L-Tyr-(Gly/L-Pro)-Gly-L-Phe-L-Leu Beads Bearing Identifier Oligos (III and I/II)

Beads from (b) and (c) are pooled and divided into two equal portions. One portion is treated as in (b), substituting Fmoc(OtBu)-L-Tyr-OH and Oligo (III) as appropriate.

E. Preparation of L-Pro-(Gly/L-Pro)-Gly-L-Phe-L-Leu Beads Bearing Identifier Oligos (IV and I/II)

The second pool is treated as before, substituting Fmoc-L-Pro-OH and Oligo (IV) as appropriate.

F. Reconstitution and Deprotection of the Peptide Library

Beads from (d) and (e) are pooled, and the phosphate, amino acid side-chain, and nucleotide exocyclic amino protecting groups are removed as follows. A one hour treatment with a 1:2:2 mixture of thiophenol:triethylamine:p-dioxane is followed by washing the beads with methanol (2×) and then methylene chloride (2×), and then the beads are treated for 5 min. with 95:5 trifluoroacetic acid:ethanedithiol. After a wash with methanol (3×), the beads are treated at 55 degrees C. with 1:1 ethylenediamine:ethanol for 1 hour and then washed first with ethanol (2×) and then with PBS (2×). This collection of beads constitutes the library and contains approximately equal quantities of the 4 immobilized peptides YGGFL, YPGFL, PGGFL and PPGFL. Additionally, each bead carries two distinct 113 bp oligonucleotide sequences encoding the identities of both the first and second amino acids of the peptide on that bead.

G. PCR Amplification of Oligonucleotide Identifier Tag

After a FAC sort of affinity purified beads into individual 0.5 mL polypropylene tubes, 25 μl of TBS containing 0.1 μg salmon sperm DNA (as carrier) are added together with 25 μl of 2× PCR Amplification Buffer (PECI) to each tube. The 2× buffer contains: 100 mM KCl; 20 mM Tris-Cl, pH 8.4, 20 degrees C.; 6 mM MgCl$_2$; 0.4 mM dNTP's; 1 μM of 5' PCR primer; 1 μM of 3' PCR primer; and 100 units/ml Taq DNA polymerase.

After buffer addition, the sample is covered with 50 μl of mineral oil and transferred to an automated thermal cycler. In the thermal cycler, the samples are heat denatured at 95 degrees C. for 2 min., and then cycled 35 times through 3 steps: 95 degrees C./30 sec., 60 degrees C./1 min., 72 degrees C./1 min., which steps are followed by an incubation at 72 degrees C. for an additional 5 min. and then the tubes are cooled and held at 15 degrees C. until ready for processing on streptavidin beads. The mixture is heated to 95 degrees C. to denature the strands, and the biotinylated purine strand and excess 3' PCR primer are removed by addition of streptavidin-coated beads. The tubes are centrifuged at 12 K rpm for 5 min. The supernatant is used in the sequencing reactions, as described below.

H. Sequencing of PCR Amplified Oligonucleotide Tags

The amplified oligonucleotides from individual bead isolates are sequenced in a pair of reactions (using ddA or ddG as chain terminators) with either the Step #1—specific or the Step #2—specific sequencing primers.

To anneal the template and primer, for each set of two sequencing lanes, a single annealing and subsequent labeling reaction is run by combining 8.5 μl of sequencing primer (conc.=0.25 pmol/μl), 1.5 μl Sequenase™ 5× sequencing buffer (200 mM Tris HCl, pH 7.5; 100 mM MgCl$_2$; and 250 mM NaCl), and 10 μl of template DNA from the amplification supernatant above. The samples are heated for 2 minutes at 65 degrees C. and allowed to cool slowly to room temperature (approx. 10 minutes).

The labeling reaction is performed as follows. Sequenase™ (v2.0) is diluted 1:20 with TE (10 mM Tris HCl, pH 7.5; and 1 mM EDTA), and a labeling cocktail containing a 2:3.5 ratio of diluted enzyme to labeling mix (i.e., a 4:2:1 mixture of 150 nM dGTP, 0.1 M dithiothreitol, alpha-$^{35}$S-dATP, >1000 Ci/mmol) is prepared. About 5.5 μl of the cocktail are incubated with 10 μl of annealed template/primer (from (i)) at 25 degrees C. for 5 min.

The termination reactions are performed as follows. 6 μl of labeling reaction mixture are added to 5 μl of each of the appropriate dd)XTP termination reaction mixes (i.e., 80 μM dGTP, 80 μM dATP, 50 mM NaCl, and 8 μM ddGTP or 8 μM ddATP). After incubation at 37 degrees C. for 5 min., about 8 μl of Stop Solution (95% formamide, 20 mM EDTA, 0.05% bromophenol blue, and 0.05% xylene cyanol) are added to each of the termination reactions.

The sequencing gel is comprised of 6% total acrylamide (19:1 acrylamide/bis), 0.09 M Tris base, 0.09 M boric acid, 1 mM EDTA, and 7 M urea. The gel is polymerized by addition of 1.9 μl of 25% ammonium persulfate per mL and 0.72 μl of TEMED per mL of above gel solution. The gel is allowed to polymerize at least one hour and is prerun at least 20 minutes prior to sample loading. Gel plates are then maintained between 40 and 50 degrees C. prior to and during the run.

Reactions are heated to 85–95 degrees C. for 2 minutes prior to loading, and the gel is run until the bromophenol blue dye reaches the bottom of the gel. The sequences of interest run between the bromophenol and xylene cyanol markers. The information required to identify the sequence of monomers in the oligomers attached to the bead is contained in the DNA sequence information.

EXAMPLE 3

Parallel Synthesis of Peptides and Oligonucleotide Tags on Carboxyl Beads

A. Synthesis of Phosphoramidites (I)–(IV)

Figure 6:
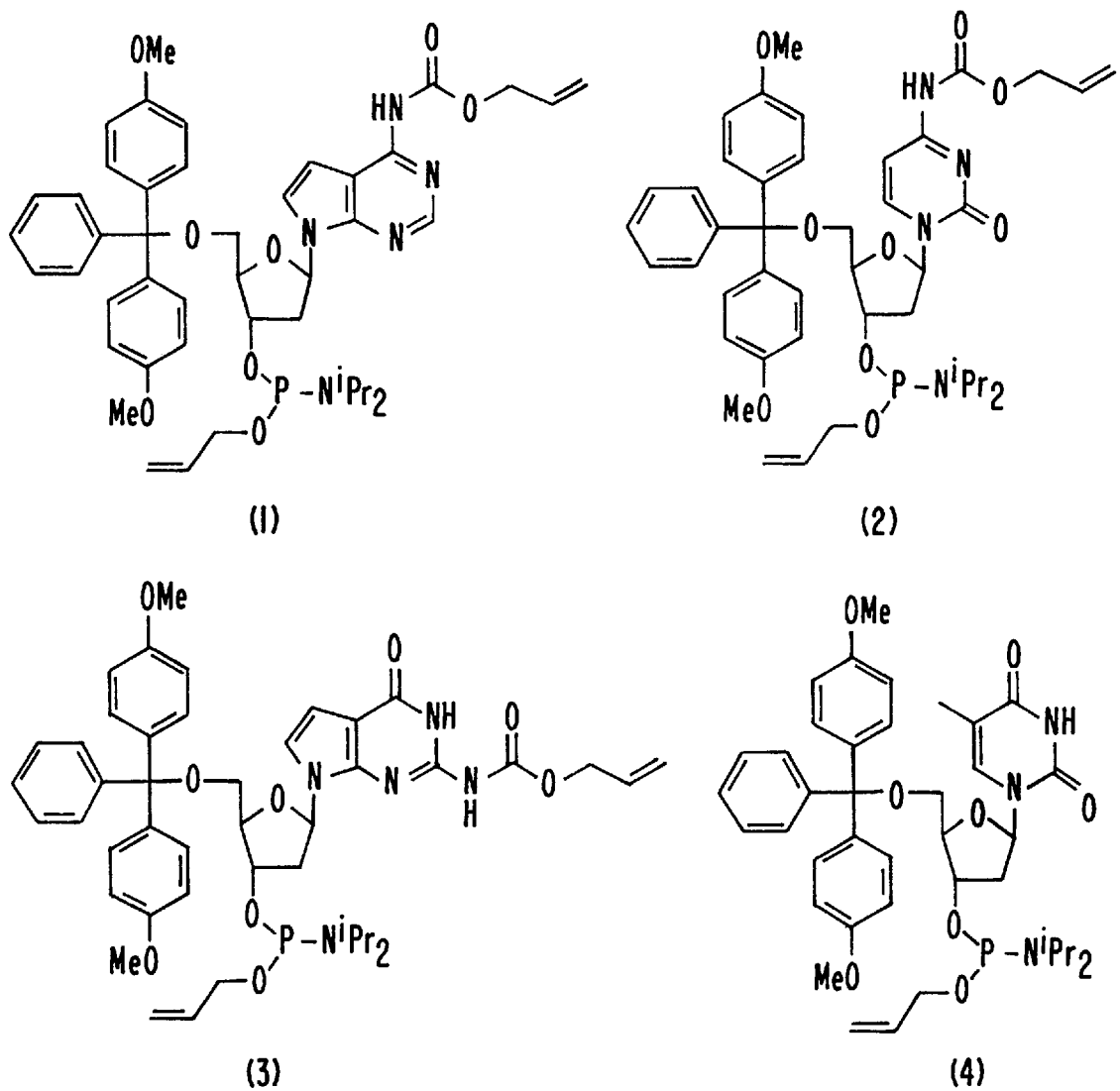
FIG. 6 illustrates 5'-DMT-3'-(O-allyl N,N'-diisopropyl phosphoramidite) nucleoside derivatives for parallel peptide/oligonucleotide synthesis.

The 3'-(allyl N,N'diisopropyl-phosphoramidites) of 5'-DMT derivatives of: (1) $N^6$-(allyloxy)carbonyl-7-deaza-2'-deoxyadenosine; (2) $N^4$-(allyloxy)carbonyl-2'-deoxycytidine; (3) $N^2$-(allyloxy)carbonyl-7-deaza-2'-deoxyguanosine; and (4) thymidine (see FIG. 6), are prepared according to the procedures of Hayakawa et al., *J. Amer. Chem. Soc.* 112: 1691–1696 (1990), incorporated herein by reference).

B. Derivatizing Carboxyl Beads With a Diamine Linker

Figure 7:
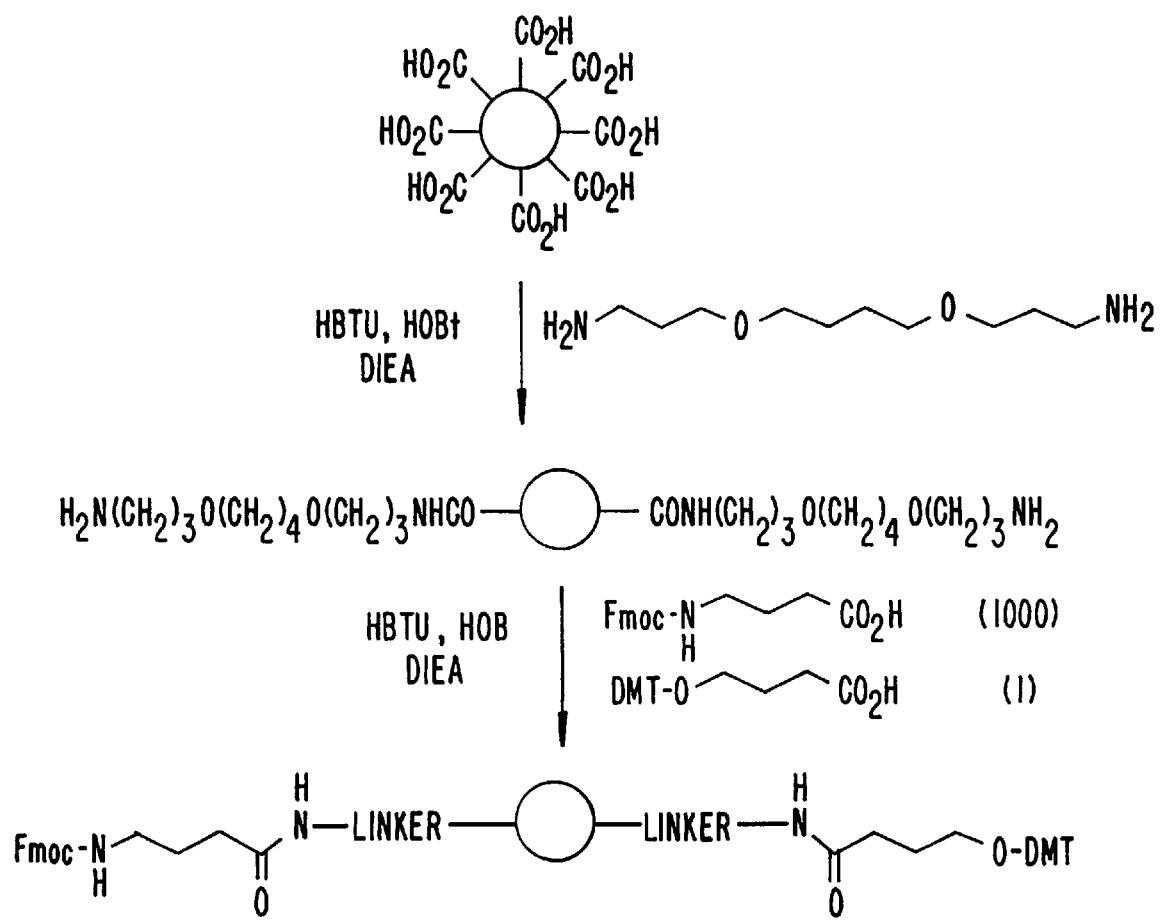
FIG. 7 illustrates the preparation of a bifunctional bead material for parallel synthesis of peptides and oligonucleotides.

Preparation of a bifunctional bead material for parallel synthesis of peptides and oligonucleotides is illustrated in FIG. 7. Three 50 mg aliquots of 4.5 µm diameter polystyrene/polydivinylbenzene/polymethylmethacrylate/COOH beads (Bangs' Laboratories) were each placed in a separate microcentrifuge tube and treated as follows. First, the beads were treated with 0.1 N aqueous HCL (3 mL) and stirred by vortexing for 15 minutes. The beads were then pelleted with a microcentrifuge, the liquid supernatant decanted, and the remaining bead pellet successively washed (by vortexing, pelleting, and decanting: a process referred to as "washed") with water (3×1 mL) and dimethylformamide (DMF, 3×1 mL).

The compounds 2-(1H-benzotriazol-1-yl)-1,1,3,3-tetramethyluronium hexafluorophosphate (HBTU, 38 mg, 0.10 mmol), 1-hydroxybenzotriazole (HOBT, 15 mg, 0.10 mmol), and DMF (0.5 mL) or dichloromethane (0.5 mL) were added to the bead pellet. Diisopropylethylamine (DIEA, 54 µl, 0.30 mmol) was added, and the suspension was vortexed for 1 min. The compound 4,9-dioxa-1,12-dodecanediamine (20 µl, 0.10 mmol) was then added, and the reaction was vortexed for 30 minutes. The reaction was then diluted with DMF (1 mL), the beads were pelleted, and the supernatant decanted. The pellet was treated with 9:1 DMF/water (1.0 mL) and vortexed for 15 minutes. The beads were then pelleted, the supernatant decanted, and the beads washed with DMF (3×1.0 mL).

C. Attaching Peptide and Oligonucleotide Synthesis Linkers 100 mg of the beads are treated with a mixture of 4-Fmoc-aminobutyric acid (0.1 mmol) and 4-p,p'-dimethoxytrityl (DMT)-hydroxybutyric acid (0.1 µmol) in the presence of HBTU (0.1 mmol), HOBt (0.1 mmol), and DIEA (0.1 mmol) in 9:1 $CH_2Cl_2$:DMF (1.0 mL). After vortex treatment for 30 minutes, the reaction mixture is diluted with DMF (1.0 mL), the beads pelleted, and the supernatant decanted. The beads are washed with DMF (3×1.0 mL). The coupling procedure is then repeated with fresh reagents, and the beads are pelleted and washed as described above.

D. Building a 3' PCR Priming Site on the Hydroxy Linkers

Figure 8:
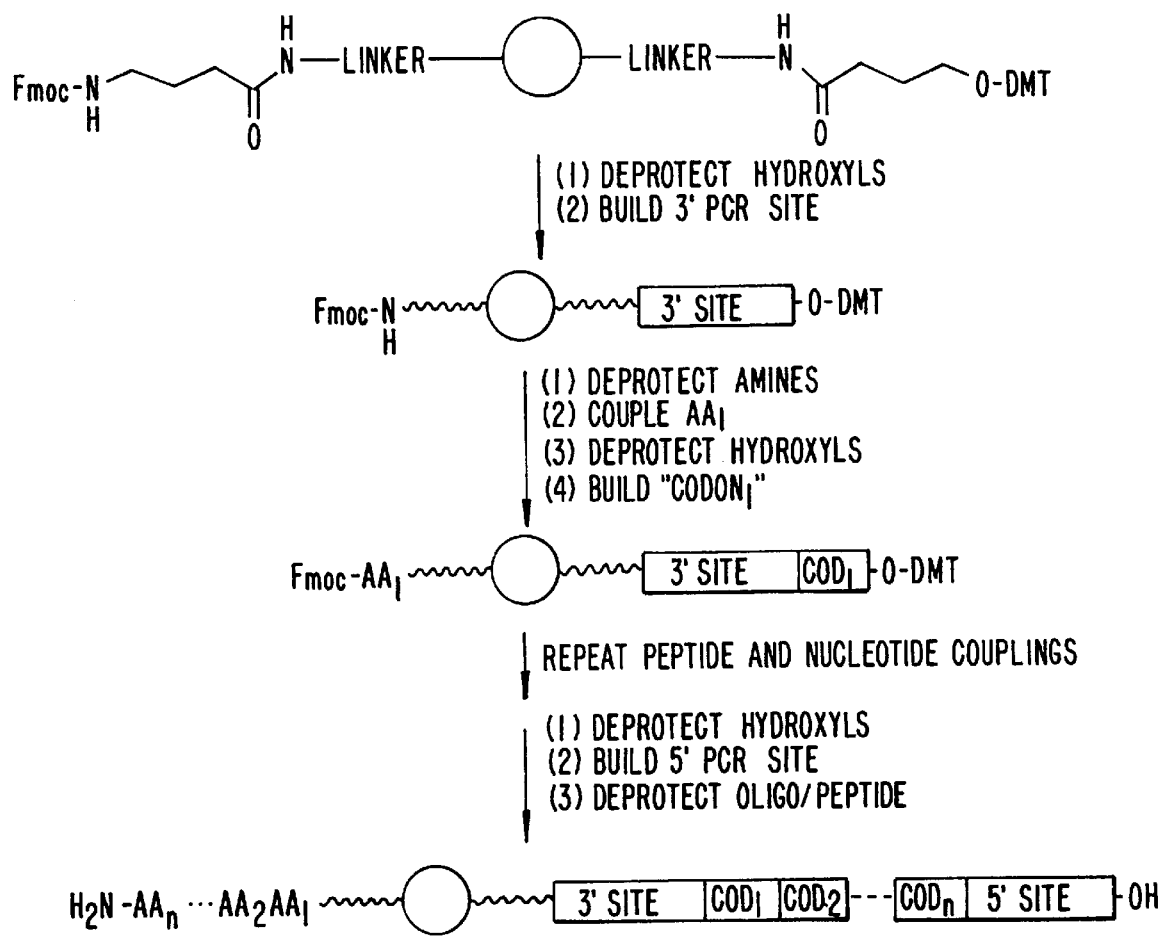
FIG. 8 illustrates the parallel assembly of oligonucleotide-tagged peptides on beads.

The parallel assembly of oligonucleotide-tagged peptides on beads is illustrated in FIG. 8. A PCR priming site of 20–25 nucleotides is assembled as follows. Note that all reagents used are anhydrous, and reactions occur under an atmosphere of dry argon. About 10 mg of the beads are subjected to an eight-step reaction sequence to couple a protected phosphoramidite. The reaction steps are: (1) beads are washed for 0.5 minutes with acetonitrile (MeCN); (2) DMT groups are removed with 3% trichloroacetic acid in $CH_2Cl_2$ for 1.5 minute; (3) beads are washed with MeCN for 3 minutes; (4) beads are treated with 0.1 M phosphoramidite (I, II, III, or IV) in MeCN containing either 0.5 M (4-nitrophenyl) tetrazole or 0.5 M pyridinium hydrochloride and 1.0 M imidazole for 2 min.; (5) beads are washed with MeCN for 0.5 minutes; (6) beads are capped with a mixture of $Ac_2O$/2,6-lutidine/THF (1:1:8) containing 5% DMAP; (7) beads are oxidized with 1 M $^tBuOH$ in $CH_2Cl_2$ for 0.8 minutes; and (8) beads are washed for 0.5 minutes with MeCN. Steps one through eight are repeated from one to 25 times to assemble a PCR priming site of up to 25 nucleotides.

E. Coupling of First Amino Acid to Amino Linkers

Peptide and nucleotide couplings may be alternated, as illustrated in FIG. 8. To couple an amino acid (or peptide), the Fmoc group is first removed from the beads by treatment with 30% piperidine in DMF for 60 min. The beads are washed 3 times with DMF. The beads are then treated with a solution containing the appropriate amino acid (0.1 M), HBTU (0.1 M), HOBt (0.1 M), and DIEA (0.1 M) in 9:1 $CH_2Cl_2$:DMF for 30 min. The coupling is then repeated with fresh reagents for a further 30 min. and the beads are washed with DMF (3×) and then with MeCN (3×).

F. Construction of First Oligonucleotide "Codon"

A "codon" of about 3 to 5 nucleotides uniquely representing the identity of the first amino acid is then built at the 5' end of the oligonucleotide chain using the 8-step coupling cycle in procedure (d) above.

G. Coupling of Subsequent Amino Acids and "Codon" Construction

The methods of procedures (e) and (f) are then repeated using the appropriate amino acid and nucleotide building blocks until the desired peptide and the oligonucleotide coding region are completely assembled.

H. Construction of a 5' PCR Priming Site

The 8-step coupling cycle of procedure (d) is used to build a 20–25 nucleotide PCR priming site on the 5' terminus of the oligonucleotide chains.

I. Deprotection of the Oligonucleotide and Peptide Chains

The fully assembled peptide and oligonucleotide chains are deprotected as follows. The amino-terminal Fmoc groups are removed by treatment with 30% piperidine in DMF and then a wash with THF (3×). To remove the allylic protecting groups, the beads are treated with a THF solution containing tris(dibenzylideneacetone) dipalladium-chloroform complex (0.02 M), triphenylphosphine (0.2 M), and 1:1 n-butylamine/formic acid (1.2 M) at 50° C. for 30 min. and the pelleted beads are washed with THF. The beads are washed with 0.1 M aqueous sodium N,N-diethyldithiocarbamate and then water to remove traces of palladium. The amino acid protecting groups are then removed by treatment with 95:5 TFA/water for 30 min. "Scavenger" reagents such as 1,2-ethanedithiol and thioanisole may also be included in this acidic deprotection medium (e.g., 2% of each by volume). Finally, the fully deprotected beads are washed with aqueous buffer and are ready for interaction with a biological receptor.

EXAMPLE 4

Library Preparation and Screening

In this example, two populations of amine derivatized beads were labeled with oligonucleotides possessing base sequences uniquely characteristic of each bead population. The population labeled with an oligonucleotde 95 bases in length (95 mer) was subsequently coupled to the peptide YGGFL. The population of beads labeled with an oligonucleotide 110 bases in length (110 mer) was coupled to phenyalanine (F). The beads were then mixed in the ratio of twenty F/110 mer beads for each YGGFL/95 mer bead and stained with a fluorescently labeled antibody 3E7 that binds the peptide YGGFL with high affinity. Individual fluorescently stained beads could then be sorted by FACS directly into PCR tubes. After PCR, 5 of 6 fluoresently stained beads gave rise to a fragment of amplified DNA 95 bp long. PCR of the remaining single bead gave rise to small DNA fragments, possibly being primer dimer.

The oligonucleotides used in this experiment are the two tags, two PCR primers, and one sequencing primer. The same PCR and sequencing primers were used for the two tags. The two tags differ in their sequence and length. Both tags were composed of the bases 7-deazaA, C, and T.

The 95 mer tag has the sequence:
CCA CTC ACT ACC ACT CTA CTA TAA CCA CCC CTT CCT ATT CCA AAA TTA CAA Act tat ctc aac tac atc t<u>CA CAC TCA CTC ATC TCT ACA TCT AC</u> (SEQ ID NO:8)

The 110 mer tag has the sequence:
<u>CCA CTC ACT ACC ACT CTA CTA TAA CCC</u> TCC CCT ATT CCA AAA TTA CAT CCT ATT CCA AAA TTA CAA Act tat ctc aac tac atc t <u>CA CAC TCA CTC ATC TCTACA TCT AC</u> (SEQ ID NO:9)

For each target the underlined sequences represent PCR primer binding sites: the sense primer is at the 5'-end, and the anti-sense primer is at the 3'-end. Also, for each target the small case sequence represents the sequencing primer binding site.

A. Bead Preparation

Beads were purchased from Bang's Laboratories (979 Keystone Way, Carmel, Ind. 46032) and are composed of carboxylated polystyrene (4.5 μm average diameter). These beads were subjected to diamine derivitization by the process described below.

Beads (200 mg) were treated with 1.0 mL of 1 N HCl and vortexed 15 min. The beads were pelleted, decanted, and washed with three times (3×) with 1.0 mL of water each wash and then washed 3× with 1.0 mL of DMF each wash. To the washed pellet was added 2-(1H-benzotriazol-1-yl)-1,1,3,3-tetramethyluronium hexafluorophosphate (HBTU; 38 mg, 0.1 mmole), 1-hydroxybenzotriazole hydrate (HOBT; 15 mg, 0.1 mmole), 500 μL of methylene chloride, and 54 μL of diisopropylethylamine (DIEA; 0.3 mmole). After vortex treatment for 2 min., 20 μL of diamine (4,9-dioxa-1,12-dodecanediamine; 94 μmole) were added. After vortex treatment for 30 min, 1.0 mL of DMF was added, and the beads were pelleted by centrifugation. The supernatant was removed, and 1.0 mL of 10% water in DMF was added. The beads were vortexed an additional 15 min. and finally washed 3× with 1.0 mL of DMF each wash.

B. Oligonucleotide Attachment

Two different target oligonucleotides were employed in this experiment: a 95 mer and a 110 mer. These oligonucleotides were composed of the bases cytidine, thymidine, and 7-deaza adenosine. The oligonucleotides were synthesized with a primary amino group on the 5'-terminus (5'-amino modifier C-12, Glen Research). Lyophilized oligonucleotide (600 pmole) was dissolved in 5 μL of 0.5 M Na-phosphate, pH 7.7, and the solution was treated with 10 μL of 0.2 M disuccinimydylsuberate (DSS). The reaction proceeded 10 min., and then 85 μL of ice-cold water were added. Unreacted DSS was removed by centrifugation. The supernatant was passed through a G25 spin column that had been equilibrated with water. The eluant was immediately frozen and lyophilized to isolate the 5'-N-hydroxysuccinamide ester of the oligonucleotide.

This activated oligonucleotide was dissolved in 50 μL of 0.1 M Na-phosphate, pH 7.5, which contained 0.1 mg/mL of sonicated salmon sperm DNA. This solution was added to 10 mg of diamine derivitized beads. After vortex treatement for 3 hr., the beads were washed 2× with 0.4 mL of 0.1 M Na-phosphate, pH 7.5, each wash, and then washed 2× with 0.4 mL of 0.1 N NaOH. Finally, the beads were washed with 3× with 0.4 mL of pH 7.5 buffer.

C. Peptide Attachment

To Boc-YGGFL or Boc-Phe (Boc=t-butoxy-carbonyl amine protecting group; 0.1 mmole) was added HBTU (0.1 mmole), HOBT (0.1 mmole), 1.0 mL of 10% DMF in methylene chloride, and DIEA (0.3 mmole). After vortex treatment to dissolve the solids, 0.4 mL of the peptide solution was added to 3 mg of oligonucleotide-labeled beads. The solution containing Boc-YGGFL was added to beads labeled with the 95 mer, and the solution containing Boc-Phe was added to beads labeled with the 110 mer. The reaction mixtures were vortexed 30 min. and then diluted with DMF, centrifuged, decanted, and the bead pellets washed with 3× with 1.0 mL of THF. The Boc protecting groups were removed by treating the beads with 0.4 mL of 95% trifluoroacetic acid for 10 min. The deprotection reaction was then diluted with THF, centrifuged, and decanted, and the beads were washed with 3× with 1.0 mL of DMF each wash. Finally, the beads were washed with 3× with 0.5 mL of 0.1 M Na-phosphate, pH 7.5, each wash and stored as a slurry (10 mg/mL).

D. Mixing, Staining, and Sorting

The beads coupled with the 95 mer and YGGFL were mixed with the beads that were coupled to the 110 mer and F in the ratio of 1:20. Thus, 0.1 mg of 95 mer/YGGFL beads (2 million beads) were mixed with 2.0 mg of the 110 mer/Phe beads (40 million beads). The mixture was suspended in blocking buffer (PBS, 1% BSA, and 0.05% Tween-20) and incubated at room temperature for 1 hr. The beads were next pelleted by centrifugation and resuspended in a solution of an FITC-labeled monoclonal antibody 3E7 that binds the peptide YGGFL (1 μg/mL). The suspension was incubated 0.5 hr on ice and then centrifuged to isolate the bead pellet.

The beads were resuspended in PBS for delivery into the fluorescence activated cell sorting (FACS) instrument (Becton Dickinson FACSORT Plus). Beads that had bound to the fluorescently labeled antibody were identified by their acquired fluorescence, and fluorescent beads were isolated by sorting into PCR tubes. One, ten, or one hundred fluorescent beads were sorted into each PCR tube. In an analogous manner, non-fluorescent beads were also sorted into PCR tubes.

E. Amplification of Sorted Beads

To each PCR tube containing a bead or beads was added 25 μL of PCR buffer (20 mM Tris-HCl, pH 8.7; 10 mM KCL; 10 mM $(NH4)_2SO_4$; 2 mM $MgCl_2$; 0.1% Triton X-100; 0.14 mg/mL BSA; 200 μm dATP; 200 μm dGTP; 200 μm dCTP; 200 μm dTTP; 2 μm primer #1; 2 μm primer #2; and 0.5 units of Pfu DNA polymerase). Reactions were subjected to 40 cycles of 95° C. for 0.5 min., 55° C. for 1 min., and 72° C. for 1 min.

Gel loading dye (2 μL) was added to 10 μL of each PCR, and the sample was run on a 2% low melting point agarase gel. DNA fragments were visualized by staining with ethidium bromide and exposure to UV light. Five of six of the tubes containing single flourescent beads gave rise to DNA fragments 95 base pairs in length, confirming that these beads were coupled to YGGFL and not F. Tubes containing 10 or 100 fluorescent beads also gave rise to 95 mer DNA fragments. Conversly, none of the tubes containing 1, 10, or 100 non-fluorescent beads gave rise to 95 mer fragments.

There were, however, anomalous amplification products smaller than 110 bp from amplification of the tags of non-fluorescent beads. These anomalous products may have arisen through the use of unprotected oligonucleotide tags in this example, which may have allowed the free exocyclic amines to couple to the F amino acid, thereby rendering the tag subject to anomalous amplification. This problem would not have affected the 95 mer tag to the same extent, because YGGFL would be less reactive with the exocyclic amines than F.

EXAMPLE 5

Library Synthesis and Screening

Figure 9:
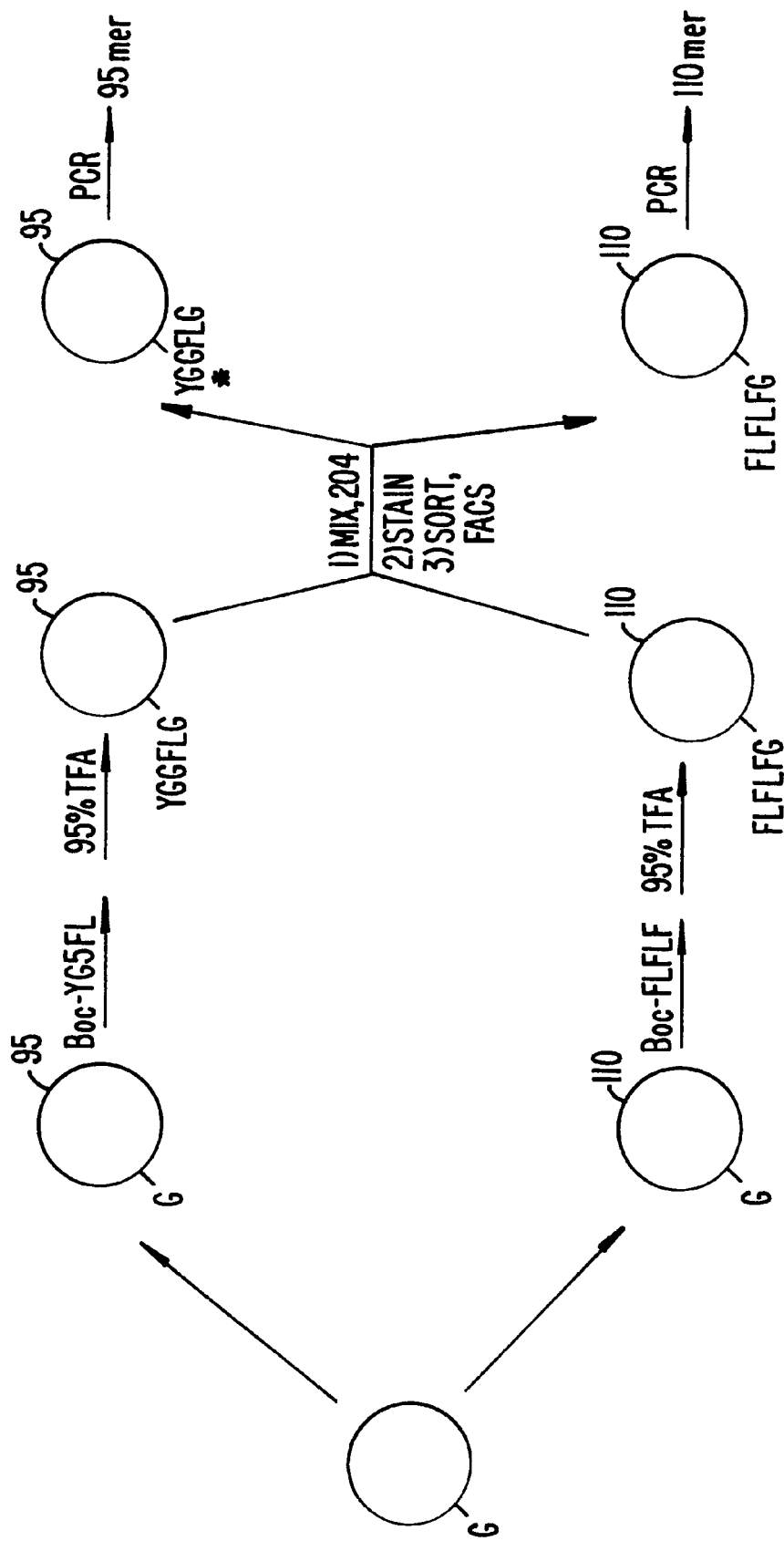
FIG. 9 shows a schematic representation of the experiment described in Example 5, in which two populations of oligomers on beads are prepared, tagged, mixed, sorted, and identified by the method of the present invention.

This example is illustrated schematically in FIG. 9. Briefly, a single population of amine derivatized beads (prepared as described in Example 4) was coupled to glycine. The population was then divided into two equal parts, and each part was labeled with a characteristic oligonucleotide that would uniquely identify the bead subpopulation. The subpopulation that had been labeled with an oligonucleotde 95 bases in length (the 95 mer described in Example 4) was subsequently coupled to the peptide YGGFL. The population of beads that had been labeled with an oligonucleotide 110 bases in length (the 110 mer described in Example 4) was coupled to the peptide FLFLF (SEQ ID NO:16). The beads were then mixed in the ratio of twenty FLFLF/110 mer beads for each YGGFL/95 mer bead (i.e., 20:1) and stained with a fluorescently labeled antibody (3E7) that binds the peptide sequence YGGFL with high affinity. Individual fluorescently stained beads and unstained beads were sorted directly into PCR tubes. Upon PCR, all the fluoresently stained beads gave rise to a fragment of amplified DNA 95 base pairs in length, and all the unstained beads gave rise to a fragment 110 base pairs in length.

A. Peptide Coupling Step #1

To Fmoc-Gly (Fmoc=9-fluorenylmethoxycarbonyl amine protecting group; 0.1 mmole) was added HBTU (0.1 mmole), HOBT (0.1 mmole), 1.0 mL of 10% DMF in methylene chloride, and DIEA (0.3 mmole). After vortex treatment to dissolve the solids, 0.4 mL of the solution containing the activated amino acid was added to 50 mg of diamine derivatized beads. The reaction mixture was vortexed 30 min. and then diluted with DMF, centrifuged, decanted, and the bead pellet washed twice with 1.0 mL of DMF. The coupling reaction was then repeated. The beads were then treated with 1.0 mL of 30% piperidine in DMF with vortexing for 1 hr. to deprotect the glycine amino group.

B. Oligonucleotide Labeling

Two different target oligonucleotides were employed in this experiment: the 95 mer and 110 mer described in Example 4. Half of the bead sample described above (25 mg) was labeled with the 95 mer, and the other half was labeled with the 110 mer. These oligonucleotides are composed of 2'-deoxy-cytidine, thymidine, and 2'-deoxy-7-deaza-adenosine. The oligonucleotides were synthesized with a primary amino group on the 5'-terminus (MMT-C12-Aminomodifier, Clonetech Laboratories, Inc.). Lyophilized oligonucleotide (1.5 nmole) was dissolved in 10 µL of 0.5 M Na-phosphate, pH 7.7, and the solution was then treated with 20 µL of 0.2 M disuccinimydylsuberate (DSS). The reaction proceeded 10 min., and then, 70 µL of ice-cold water were added. Unreacted DSS was removed by centrifugation. The supernatant was passed through a G-25 spin column that had been equilibrated with water. The eluant was immediately frozen and lyophilized to isolate the 5'-N-hydroxysuccinamide ester of the oligonucleotide. This activated oligonucleotide was dissolved in 100 µL of 0.1 M Na-phosphate, pH 7.5, which contained 0.1 mg/mL of sonicated salmon sperm DNA. This solution was added to 25 mg of glycine-coupled beads. After vortex treatment for 3 hr., the beads were washed twice with 0.4 mL of 0.1 M Na-phosphate, pH 7.5, and twice with 0.4 mL of 0.1 N NaOH. Finally, the beads were washed three times with 0.4 mL of pH 7.5 buffer.

C. Peptide Coupling Step #2

To Boc-YGGFL or Boc-FLFLF (Boc=t-butoxy-carbonyl amine protecting group; 0.02 mmole) was added HBTU (0.02 mmole), HOBT (0.02 mmole), 0.190 mL of 10% DMF in methylene chloride, and DIEA (0.06 mmole). After vortextreatment to dissolve the solids, the solution was diluted ten-fold in 10% DMF in methylene chloride. An aliquot of this solution (0.345 mL) was added to the glycine-coupled and oligonucleotide-labeled beads (25 mg). The solution containing Boc-YGGFL was added to beads labeled with the 95 mer, and the solution containing Boc-FLFLF was added to beads labeled with the 110 mer. The reaction mixtures were vortexed 30 min. and then diluted with DMF, centrifuged, decanted, and the bead pellets washed three times with 1.0 mL of THF. The Boc protecting groups were removed by treating the beads with 0.4 mL of 95% trifluoroacetic acid for 10 min. The deprotection reaction was then diluted with THF, centrifuged, decanted, and the beads washed three times with 1.0 mL of DMF. Finally, the beads were washed three times with 0.5 mL of 0.1 M Na-phosphate, pH 7.5, and stored as a slurry (10 mg/mL).

D. Mixing, Staining, and Sorting

The beads coupled to the 110 mer and FLFLF were mixed with the beads that were coupled to the 95 mer and YGGFL in the ratio of 20:1. Thus, 0.1 mg of 95 mer/YGGFL beads (2 million beads) were mixed with 2.0 mg of the 110 mer/FLFLF beads (40 million beads). The mixture was suspended in blocking buffer (PBS, 1% BSA, 0.05% Tween-20) and incubated at room temperature for 1 hr. The beads were next pelleted by centrifugation and resuspended in a solution of an FITC-labeled monoclonal antibody (3E7) that recognizes the peptide sequence YGGFL (1 µg/mL). The suspension was incubated 0.5 hr. on ice and then centrifuged to isolate the bead pellet.

Figure 10:
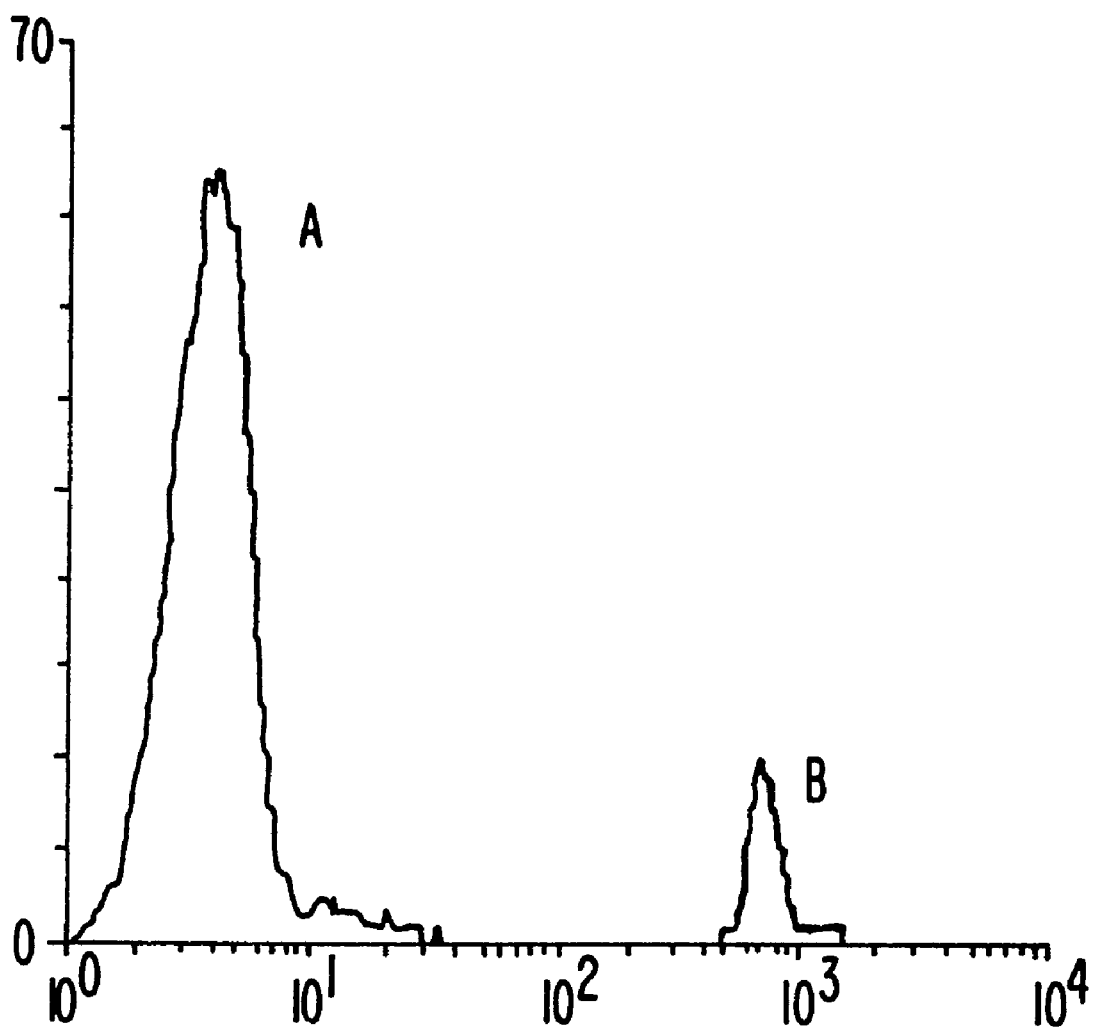
FIG. 10 shows resolution of the two populations of beads by FACS in the experiment described in Example 5. Values along the horizontal axis indicate relative fluorescence (log scale). Values along the vertical axis indicate relative numbers of beads. Non-fluorescently labeled beads are represented by peak A. Flourescently labeled beads are represented by peak B. The ratio of the larger peak to the smaller peak is 15:1.

The beads were resuspended in PBS for delivery into the fluorescence activated cell sorting (FACS) instrument (Becton Dickinson FACSORT Plus). Beads that had bound to the fluorescently labeled antibody were identified by their acquired fluorescence (see FIG. 10), and homogeneous samples of either fluorescent or non-fluorescent beads were isolated by sorting into PCR tubes. One, ten, or one hundred beads of each type were sorted into each PCR tube.

E. PCR of Sorted Beads

Figure 11A:
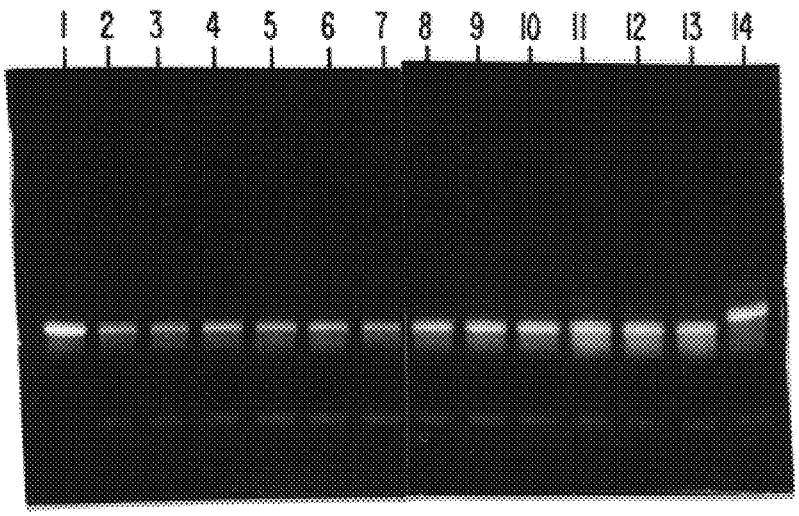
FIG. 11 shows pictures of ethidium bromide stained, UV irradiated agarose gels of PCR products obtained by amplification after FACS of two bead populations and amplification of the tags on the sorted beads, with controls, as described in Example 5. Gel A shows the results with sorted fluorescent beads: lane 1—$2.4 \times 10^6$ copies (100 bead equivalents) of 95 mer tag; lanes 2–7—PCR product from single fluorescent beads; lanes 8–10—PCR product from ten fluorescent beads; lanes 11–13—PCR product from one hundred fluorescent beads; and lane 14—$1.2 \times 10^6$ copies (100 bead equivalents) of 110 mer tag. Gel B shows the result with sorted non-fluorescent beads: lane 1—$1.2 \times 10^6$ copies of 110 mer tag; lanes 2–7—PCR product from single non-fluorescent beads; lanes 8–10—PCR product from ten non-fluorescent beads; lanes 11–13—PCR product from one hundred non-fluorescent beads; and lane 14—$2.4 \times 10^6$ copies of 95 mer tag. Gel C shows the results with the control reactions: lanes 1,12—DNA size standards; lanes 2, 3—no tag control reactions; lanes 4, 5—1 bead equivalent of soluble 95 mer tag; lanes 6, 7—10 bead equivalents of soluble 95 mer tag; lanes 8, 9—1 bead equivalent of soluble 110 mer tag; and lanes 10, 11—10 bead equivalents of soluble 110 mer tag.
Figure 11B:
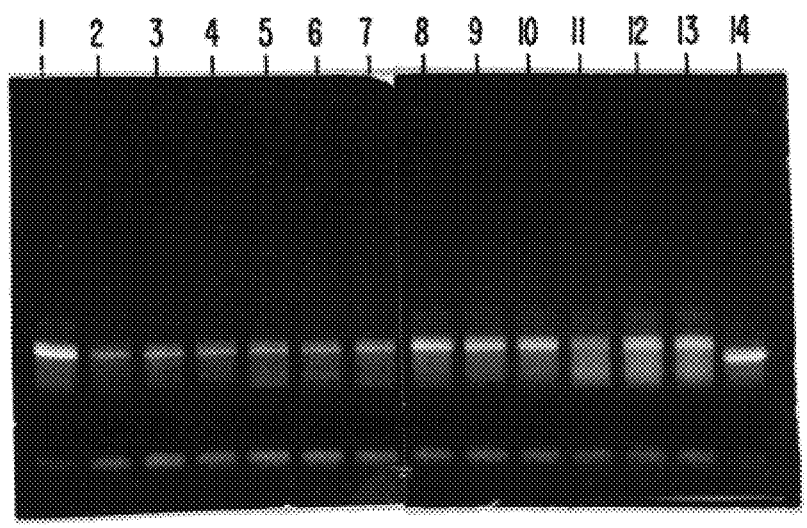
Figure 11C:
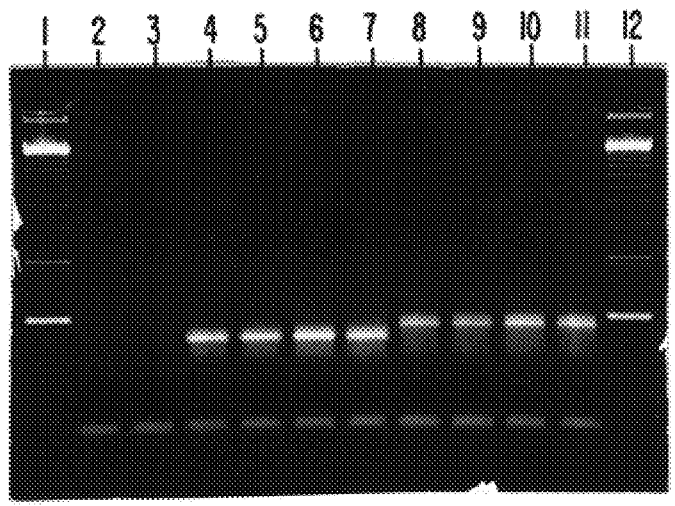

To each PCR tube containing a bead, or beads, was added 25 µL of PCR mix (20 mM Tris-HCl, pH 8.7, 10 mM KCL, 10 mM $(NH_4)_2SO_4$, 2 mM $MgCl_2$, 0.1% Triton X-100, 0.14 mg/mL BSA, 200 µM dATP, 200 µM dGTP, 200 µM dCTP, 200 µM dTTP, 2 µM of each primer (as described in Example 4), and 0.5 units of Pfu DNA polymerase). Reactions were subjected to 40 cycles of 95° C. for 0.5 min., 55° C. for 1 min., and 72° C. for 1 min. Gel loading dye (2 µL) was added to 10 µL of each PCR and the sample run on a 2% low melting point agarose gel. DNA fragments were visualized by staining with ethidium bromide and exposure to UV light. Six single bead samples, three 10 bead samples, and three 100 bead samples were amplified from both the fluorescent and non-fluorescent populations. All the bead samples from the flourescent population produced only DNA fragments 95 base pairs in length, and all the samples from the non-fluorescent population produced only fragments 110 base pairs in length (see FIG. 11).

We claim:

1. A bifunctional solid support having a plurality of amine active sites and a plurality of hydroxyl active sites.

2. The solid support of claim 1, wherein said solid support is a polystyrene/polydivinylbenzene/polymethylmethacrylate COOH bead.

3. The solid support of claim 1, wherein said amine active sites are blocked with a first protecting group and said hydroxyl active sites are blocked with a second protecting group, wherein said first and second protecting groups are orthogonal.

4. The solid support of claim 3, wherein said bifunctional solid support is produced by:

(a) derivatizing polystyrene/polydivinylbenzene/polymethylmethacrylate COOH beads with a 4,9-dioxa-1,12-dodecanediamine linker; and (b) treating said beads with 4-Fmoc-aminobutyric acid and 4-p,p'-dimethoxytrityl-hydroxybutyric acid in the presence of HBTU, HOBt and DIEA.

5. The solid support of claim 3, wherein said first protecting group is an Fmoc group.

6. The solid support of claim 3, wherein said second protecting group is a dimethoxytrityl group.

7. The solid support of claim 1, wherein said solid support is a polystyrene bead.

8. The solid support of claim 1, wherein said solid support is a silica bead.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
       (A) LENGTH: 111 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

CTTTCTTCCT CTCCCTCTTT TCTCCTCTCT TTTTTTCTCC TTCTTTTTTT CTCTCCCTCT     60

CTCCTCTCTC CCCTTTCTCT CCTTTCCTCC TCTCCTCTCT CTCTTCTTTC C             111

(2) INFORMATION FOR SEQ ID NO:2:

(i) SEQUENCE CHARACTERISTICS:
       (A) LENGTH: 111 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

CTTTCTTCCT CTCCCTCTTT TCTCCTCTTC TTTTTTCTCC TTTCTTTTTT CTCTCCCTCT     60

CTCCTCTCTC CCCTTTCTCT CCTTTCCTCC TCTCCTCTCT CTCTTCTTTC C             111

(2) INFORMATION FOR SEQ ID NO:3:

(i) SEQUENCE CHARACTERISTICS:
       (A) LENGTH: 115 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:3:

CTTTCTTCCT CTCCCTCTTT TCTCCTCTTT CTTTTTCTCC TTTTCTTTTT CTCTCCCTCT     60

CTCCTCTCTC TCTTCCTTTC CCCTCTCTCT CTCCTCTCCT CTCTCTCTTC TTTCC         115

(2) INFORMATION FOR SEQ ID NO:4:

(i) SEQUENCE CHARACTERISTICS:
       (A) LENGTH: 115 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:4:

CTTTCTTCCT CTCCCTCTTT TCTCCTCTTC TTTTTTCTCC TTTCTTTTTT CTCTCCCTCT     60

CTCCTCTCTC TCTTCCTTTC CCCTCTCTCT CTCCTCTCCT CTCTCTCTTC TTTCC         115

(2) INFORMATION FOR SEQ ID NO:5:

(i) SEQUENCE CHARACTERISTICS:

(A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGAAAGAAGA GAGAGAGGAG AGG                                              23

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AGAGAGGGGA AAGGAAGA                                                    18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

AGGAAAGGAG AGAAAGGG                                                    18

(2) INFORMATION FOR SEQ ID NO:8:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CCACTCACTA CCACTCTACT ATAACCACCC CTTCCTATTC CAAAATTACA AACTTATCTC      60

AACTACATCT CACACTCACT CATCTCTACA TCTAC                                 95

(2) INFORMATION FOR SEQ ID NO:9:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CCACTCACTA CCACTCTACT ATAACCCTCC CCTATTCCAA AATTACATCC TATTCCAAAA      60

TTACAAACTT ATCTCAACTA CATCTCACAC TCACTCATCT CTACATCTAC                110

(2) INFORMATION FOR SEQ ID NO:10:

(i) SEQUENCE CHARACTERISTICS:

(A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:10:

Gly Gly Phe Leu
1

(2) INFORMATION FOR SEQ ID NO:11:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:11:

Pro Gly Phe Leu
1

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:12:

Tyr Gly Gly Phe Leu
1               5

(2) INFORMATION FOR SEQ ID NO:13:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:13:

Tyr Pro Gly Phe Leu
1               5

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:14:

Pro Gly Gly Phe Leu
1               5

(2) INFORMATION FOR SEQ ID NO:15:

(i) SEQUENCE CHARACTERISTICS:
        (A) LENGTH: 5 amino acids
        (B) TYPE: amino acid
        (D) TOPOLOGY: linear

```
    (ii) MOLECULE TYPE: peptide (xi) SEQUENCE DESCRIPTION: SEQ ID NO:15:

Pro Pro Gly Phe Leu
1               5

(2) INFORMATION FOR SEQ ID NO:16:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:16:

Phe Leu Phe Leu Phe
1               5
```